(12) United States Patent
Romano et al.

(10) Patent No.: US 11,452,637 B2
(45) Date of Patent: Sep. 27, 2022

(54) SWEEPING OPTICAL SCANNER OF AN APPARATUS FOR CUTTING-OUT A HUMAN OR ANIMAL TISSUE

(71) Applicants: KERANOVA, Saint Etienne (FR); CENTRE NATIONAL DE LA RECHERCHE SCIENTIFIQUE, Paris (FR); UNIVERSITE JEAN MONNET SAINT ETIENNE, Saint-Etienne (FR)

(72) Inventors: Fabrizio Romano, Beynost (FR); Aurelien Bernard, Saint Etienne (FR); Cyril Mauclair, Planfoy (FR); Emmanuel Baubeau, Saint Etienne (FR)

(73) Assignees: KERANOVA, Saint Etienne (FR); CENTRE NATIONAL DE LA RECHERCHE SCIENTIFIQUE, Paris (FR); UNIVERSITE JEAN MONNET SAINT ETIENNE, Saint Etienne (FR)

( * ) Notice: Subject to any disclaimer, the term of this patent is extended or adjusted under 35 U.S.C. 154(b) by 122 days.

(21) Appl. No.: 16/091,881

(22) PCT Filed: Apr. 6, 2017

(86) PCT No.: PCT/EP2017/058225
§ 371 (c)(1),
(2) Date: Oct. 5, 2018

(87) PCT Pub. No.: WO2017/174711
PCT Pub. Date: Oct. 12, 2017

(65) Prior Publication Data
US 2020/0030145 A1 Jan. 30, 2020

(30) Foreign Application Priority Data

Apr. 6, 2016 (FR) ...................................... 1653038
Apr. 6, 2016 (FR) ...................................... 1653039
(Continued)

(51) Int. Cl.
*A61F 9/008* (2006.01)

(52) U.S. Cl.
CPC ........ *A61F 9/00827* (2013.01); *A61F 9/0084* (2013.01); *A61F 9/00825* (2013.01);
(Continued)

(58) Field of Classification Search
CPC ................ A61F 9/0084; A61F 9/00827; A61F 9/00825; A61F 2009/0087; A61F 2009/00872; A61F 2009/00897
See application file for complete search history.

(56) References Cited

U.S. PATENT DOCUMENTS 6,552,301 B2   4/2003  Herman et al.
8,186,357 B2   5/2012  Lubatschowski et al.
(Continued)

FOREIGN PATENT DOCUMENTS

CA        2842474 A1      2/2013
DE   102007019812 A1    10/2008
(Continued)

OTHER PUBLICATIONS

Sinclair et al., "Interactive application in holographic optical tweezers of a multi-plane Gerchberg-Saxton algorithm for three-dimensional light shaping", Optics Express vol. 12, Issue 8, pp. 1665-1670 (2004) •https://doi.org/10.1364/OPEX.12.001665.
(Continued)

*Primary Examiner* — Lynsey C Eiseman
*Assistant Examiner* — Amanda L. Steinberg
(74) *Attorney, Agent, or Firm* — BCF LLP

(57) ABSTRACT

The present invention relates to an apparatus for cutting-out including a device for treating a L.A.S.E.R. beam generated by a femtosecond laser (1), and positioned downstream from said femtosecond laser, the treatment device comprising:
a shaping system (3) positioned on the trajectory of said beam, for modulating the phase of the wave front of the L.A.S.E.R. beam according to a modulation set value calculated for distributing the energy of the L.A.S.E.R. beam in at least two impact points forming a pattern in its focal plane,
(Continued)

an optical focusing system (5) downstream from the shaping system, the optical focusing system comprising a concentrator module for focusing the phase-modulated L.A.S.E.R. beam in a focusing plane and a depth-positioning module for displacing the focusing plane into a plurality of cutting-out planes, a sweeping optical scanner (4) positioned between the concentrator module and the depth-positioning module for displacing the pattern in the cutting-out plane in a plurality of positions.

16 Claims, 13 Drawing Sheets

(30) Foreign Application Priority Data

Apr. 6, 2016 (FR) ........................................ 1653040
Jul. 29, 2016 (FR) ........................................ 1657386

(52) U.S. Cl.
CPC .................. *A61F 2009/0087* (2013.01); *A61F 2009/00872* (2013.01); *A61F 2009/00897* (2013.01)

(56) References Cited

U.S. PATENT DOCUMENTS

| | | |
|---|---|---|
| 8,262,647 B2 | 9/2012 | Raksi et al. |
| 8,267,925 B2 | 9/2012 | Raksi et al. |
| 8,506,559 B2 | 8/2013 | Raksi |
| 8,585,686 B2 | 11/2013 | Bergt et al. |
| 8,968,375 B2 | 3/2015 | Culbertson et al. |
| 9,033,963 B2 | 5/2015 | Vera et al. |
| 9,427,356 B2 | 8/2016 | Raksi |
| 9,456,925 B2 | 10/2016 | Kurtz et al. |
| 2010/0133246 A1* | 6/2010 | Bor ..................... B23K 26/361 219/121.72 |
| 2012/0271286 A1 | 10/2012 | Curatu et al. |
| 2013/0114927 A1 | 5/2013 | Smith et al. |
| 2014/0194862 A1 | 7/2014 | Smith et al. |
| 2014/0200566 A1 | 7/2014 | Smith |
| 2015/0094572 A1 | 4/2015 | Jang et al. |
| 2015/0250542 A1* | 9/2015 | Islam ..................... A61B 18/20 606/15 |
| 2015/0313760 A1 | 11/2015 | Telandro |
| 2016/0067095 A1 | 3/2016 | Fu et al. |
| 2016/0081747 A1* | 3/2016 | Thiel ..................... A61B 90/57 606/33 |
| 2016/0374857 A1* | 12/2016 | Fu ..................... A61F 9/00814 606/3 |

FOREIGN PATENT DOCUMENTS

| | | |
|---|---|---|
| EP | 1279386 A1 | 1/2003 |
| EP | 1790383 A1 | 5/2007 |
| EP | 1834616 A1 | 9/2007 |
| FR | 2957156 A1 | 9/2011 |
| WO | 2002094117 A1 | 11/2002 |
| WO | WO-02094117 A1 * | 11/2002 ............ A61B 18/20 |
| WO | 2009009246 A1 | 1/2009 |
| WO | 2011071776 A1 | 6/2011 |
| WO | 2016055539 A1 | 4/2016 |

OTHER PUBLICATIONS

English abstract provided for DE 10 2007 019 812.
English abstract provided for EP 1790383.
English abstract provided for EP 1834616.
English abstract provided for FR 2957156.
PCT International Search Report and Written Opinion of International Searching Authority for International Patent Application No. PCT/EP2017/058225 (10 pages).

* cited by examiner

FIG. 13
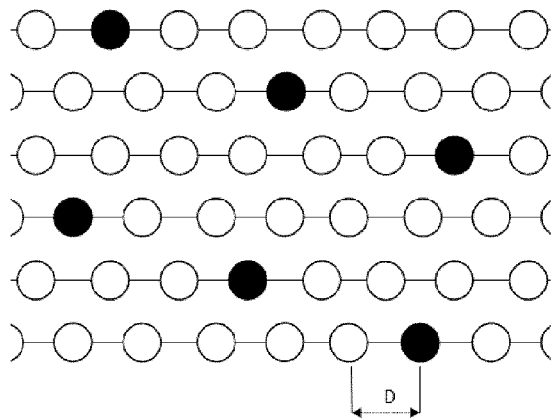
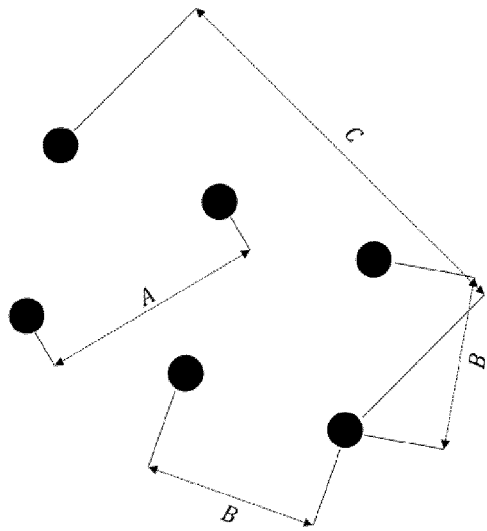
FIG. 14
$$A = D * \cos(30°) * 4$$
$$B = \sqrt{(2{,}5D)^2 + (\cos(30°) * D)^2}$$
$$C = \sqrt{(4{,}5D)^2 + (\cos(30°) * 5D)^2}$$
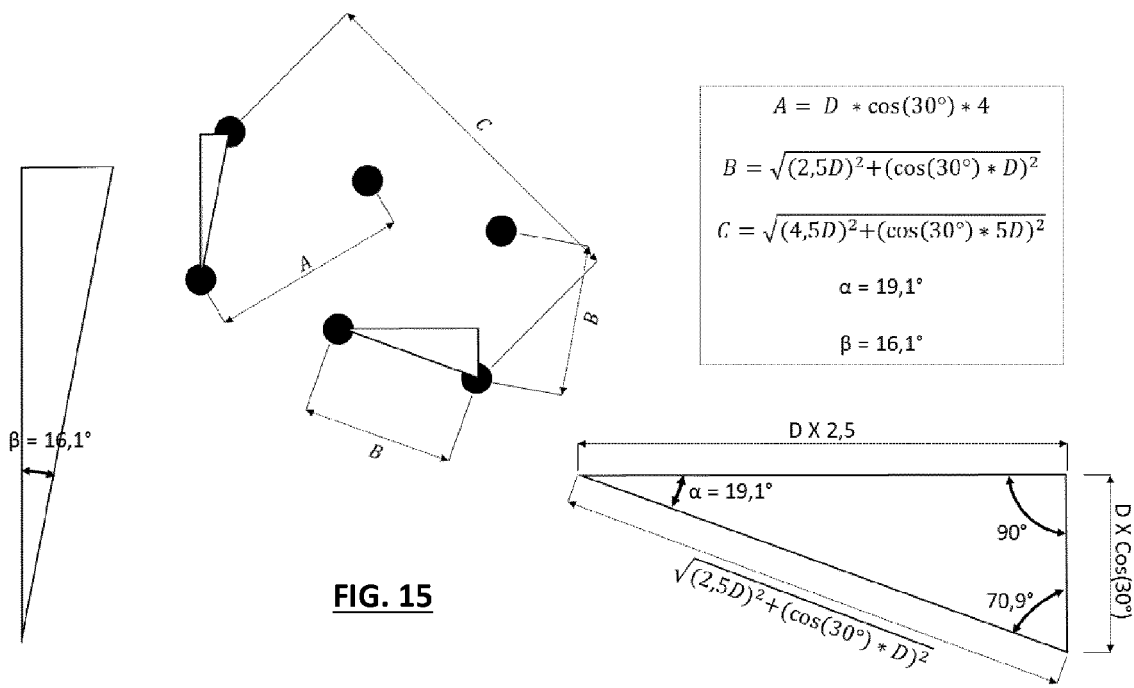
FIG. 15
$$A = D * \cos(30°) * 4$$
$$B = \sqrt{(2{,}5D)^2 + (\cos(30°) * D)^2}$$
$$C = \sqrt{(4{,}5D)^2 + (\cos(30°) * 5D)^2}$$
α = 19,1°
β = 16,1°

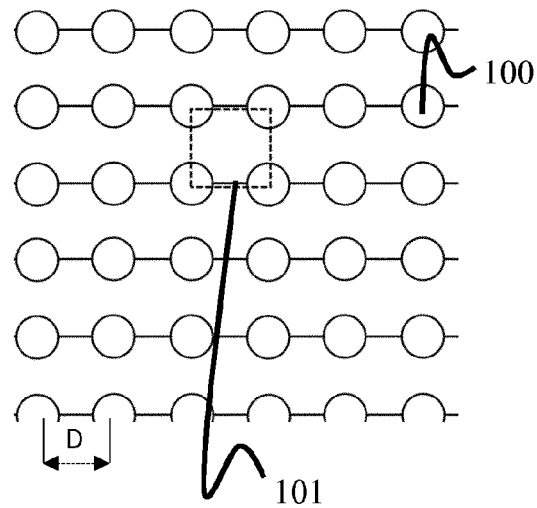
FIG. 19
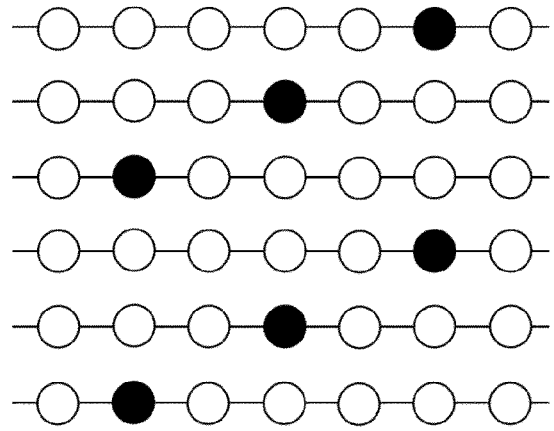
FIG. 20
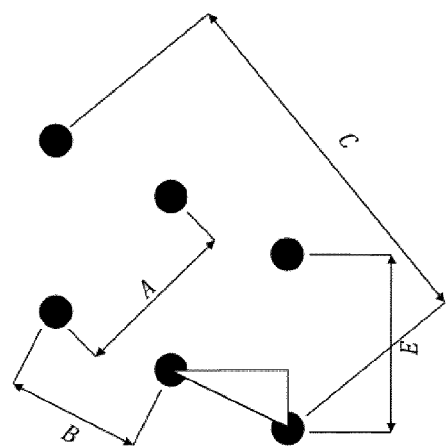
FIG. 21
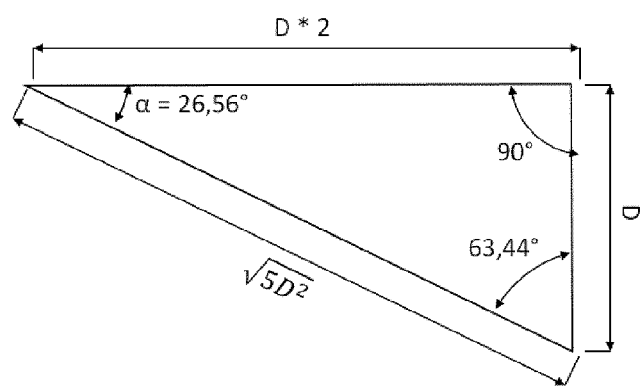

ated "portions" of the single primary L.A.S.E.R. beam.
SWEEPING OPTICAL SCANNER OF AN APPARATUS FOR CUTTING-OUT A HUMAN OR ANIMAL TISSUE

CROSS-REFERENCE TO RELATED APPLICATIONS

This application is a national phase filing under 35 U.S.C. § 371 of International Application No. PCT/EP2017/058225 filed on Apr. 6, 2017, which claims benefit of priority from French Patent Application No. 1653038 filed Apr. 6, 2016, from French Patent Application No. 1653039 filed Apr. 6, 2016, from French Patent Application No. 1653040 filed Apr. 6, 2016 and from French Patent Application No. 1657386 filed Jul. 29, 2016, the contents of which are hereby incorporated by reference in their entirety.

TECHNICAL FIELD

The present invention relates to the technical field of surgical operations made with a femtosecond laser, and more particularly that of ophthalmological surgery notably for applications for cutting-out corneas, or lenses.

The invention relates to a device for cutting-out a human or animal tissue, such as a cornea, or a lens, by means of a femtosecond laser.

By femtosecond laser, is meant a light source capable of sending a L.A.S.E.R. beam as ultra-short pulses, for which the duration is comprised between 1 femtosecond and 100 picoseconds, preferably comprised between 1 and 1,000 femtoseconds, notably of the order of about hundred femtoseconds.

PRIOR ART

From the state of the art carrying out surgical operations of the eye is known by means of a femtosecond laser, such as operations for cutting-out corneas or lenses.

The femtosecond laser is an instrument capable of achieving cutting-out of the corneal tissue for example by focusing a L.A.S.E.R. beam in the stroma of the cornea, and by making a succession of small adjacent cavitation bubbles, which then forms a cutting-out line.

More specifically, during the focusing of the L.A.S.E.R. beam in the cornea, a plasma is generated by non-linear ionization when the intensity of the laser exceeds a threshold value, called an optical breakdown threshold. A cavitation bubble is then formed, generating a very localized perturbation of the surrounding tissues. Thus, the volume actually ablated by the laser is very small comparatively with the disrupted area.

The area cut out by the laser at each pulse is very small, of the order of one micron or of tens of microns depending on the power and the focusing of the beam. Thus, a corneal lamellar cut out may only be obtained by performing a series of contiguous impacts over the whole surface of the area to be cut out.

The displacement of the beam may then be carried out with a sweeping device, consisting of controllable galvanometric mirrors, and/or plates allowing the displacement of optical elements, such as mirrors or lenses. This sweeping device gives the possibility of displacing the beam along a reciprocal trajectory along a succession of segments forming a displacement path of the beam.

In order to cut out a cornea over a surface of 1 mm², about 20,000 impacts very close to each other have to be achieved. Today, these impacts are made one by one at an average rate of 300,000 impacts/second. In order to cut out a cornea over a surface of about 65 mm², by taking into account the times during which the laser stops the production of the pulses at the end of a segment in order to allow the mirrors to be positioned on the next segment, 15 seconds on average are required. The surgical cutting-out operation is therefore slow.

In order to optimize the cutting-out time, it is known how to increase the frequency of the laser. However, increasing the frequency also involves an increase in the displacement speed of the beam, by means of suitable plates or scanners. It is also known how to increase the spacing between the impacts of the laser on the tissue to be cut out, but generally to the detriment of the cutting-out quality.

Most femtosecond lasers for corneal cut out thus use high working frequencies, generally greater than 100 kHz, associated with systems for displacing the beam combining scanners and displacement plates, which are a burden to the total cost of the facility, and therefore of the invoiced surgical operation.

In order to remedy this rapidity problem of the L.A.S.E.R. cutting-out, it is also known how to use galvanometric mirrors for increasing the rate, the speed, and the deflection trajectory of the L.A.S.E.R. beam.

However, this technique does not give entire satisfaction in terms of results.

Another solution for reducing the cutting-out time consists of generating several cavitation bubbles simultaneously.

Documents US 2010/133246, EP 1790 383 and US 2016/067095 describe cutting-out devices based on the subdivision technique of a single primary L.A.S.E.R. beam into a plurality of secondary L.A.S.E.R. beams. These devices generally comprise an optical system—such as one (or more) beam separator—to produce secondary L.A.S.E.R. beams for generating a respective cavitation bubble each.

The fact of simultaneously generating "n" cavitation bubbles gives the possibility of reducing the total duration for cutting-out a factor "n".

The leverage of a beam into several beams, with the purpose of accelerating the procedure, has already been described but always by means of purely optical solutions, either by diffraction or by multiple reflections. The result has never been utilized in a clinic, mainly since the different beams were not of a homogeneous size.

Also, the subdivision technique causes an increase in the diameter of the plurality of secondary L.A.S.E.R. beams relative to the diameter of the single primary beam L.A.S.E.R. produced by the femtosecond laser. In fact, the secondary L.A.S.E.R. beams correspond to spatially separated "portions" of the single primary L.A.S.E.R. beam. Because of the non-zero distance between the different secondary L.A.S.E.R. beams, the diameter of the assembly formed by the plurality of secondary L.A.S.E.R. beams is greater than the diameter of the primary L.A.S.E.R. beam.

This increase in diameter can be a drawback, especially in the event where the cutting-out device comprises a sweeping system—such as an optical scanner—for displacing the plurality of secondary L.A.S.E.R. beams in a cutting-out plane. In fact, the input diameter of a sweeping system is generally of the order of the diameter of the single primary L.A.S.E.R. beam such that some secondary beams do not penetrate the sweeping system.

An object of the present invention is to propose a cutting-out apparatus for eliminating at least one of the abovementioned drawbacks. In particular, an object of the present invention is to propose a cutting-out apparatus giving the possibility of producing a cutting-out plane more rapidly than with existing systems and for which the quality of the cut out is improved.

DISCUSSION OF THE INVENTION

For this purpose, the invention proposes an apparatus for cutting-out a human or animal tissue, such as a cornea or a lens, said apparatus including a femtosecond laser capable of sending a L.A.S.E.R. beam in the form of pulses and a device for treating a L.A.S.E.R. beam generated by the femtosecond laser, the treatment device being positioned downstream from said femtosecond laser, remarkable in that the treatment device comprises: a shaping system positioned on the trajectory of said beam, for modulating the phase of the wave front of the L.A.S.E.R. beam so as to obtain a phase-modulated L.A.S.E.R. single-beam according to a modulation set value calculated for distributing the energy of the L.A.S.E.R. beam in at least two impact points forming a pattern in its focal plane, an optical focusing system downstream from the shaping system, the optical focusing system comprising a concentrator module for focusing the phase-modulated L.A.S.E.R. beam in a focusing plane and a depth-positioning module for displacing the focusing plane into a plurality of cutting-out planes, a sweeping optical scanner positioned between the concentrator module and the depth-positioning module for displacing the pattern in the cutting-out plane in a plurality of positions.

Within the scope of the present invention, by "impact point" is meant an area of the L.A.S.E.R. beam, comprised in its focal plane wherein the intensity of said L.A.S.E.R. beam is sufficient for generating a cavitation bubble in a tissue.

Within the scope of the present invention, by "adjacent impact points", are meant two impact points positioned facing each other and not separated by another impact point. By "neighboring impact points" are meant two points of a group of adjacent points between which the distance is a minimum.

Within the scope of the present invention, by "pattern" is meant a plurality of L.A.S.E.R. impact points simultaneously generated in a focusing plane of a shaped L.A.S.E.R. beam—i.e. phase modulated for distributing its energy in several distinct spots in the focusing plane corresponding to the cutout plane of the device.

Thus, the invention gives the possibility of modifying the intensity profile of the L.A.S.E.R. beam in the cutout plane, so as to be able to improve the quality or else the speed of the cutting-out depending on the selected profile. This intensity profile modification is obtained by phase modulation of the L.A.S.E.R. beam.

The optical phase modulation is achieved by means of a phase mask. The energy of the incident L.A.S.E.R. beam is preserved after modulation, and the shaping of the beam is achieved by acting on its wave front. The phase of an electromagnetic wave represents the instantaneous situation of the amplitude of an electromagnetic wave. The phase depends both on the time and on the space. In the case of the spatial shaping of a L.A.S.E.R. beam, only the variation in the phase space are considered.

The wave front is defined as the surface of the points of a beam having an equivalent phase (i.e. the surface consisting of the points for which the travel times from the source having emitted the beam are equal). The modification of the spatial phase of a beam therefore requires modification of its wave front.

This technique gives the possibility of achieving the cutting-out operation in a more rapid and more efficient way since it applies several L.A.S.E.R. spots each achieving a cut out and according to a controlled profile.

In terms of the present invention, the phase modulation of the wave front generates a modulated single L.A.S.E.R. beam which forms several impact points only in the cutout plane. In this way, the modulated L.A.S.E.R. beam is single all the way along the propagation path. The phase modulation of the wave front delays or advances the phase of the different points of the surface of the beam relative to the initial wave front so that each of these points produces constructive interference at N separate points in the focal plane of a lens. This redistribution of energy into a plurality of impact points occurs in a single plane only (i.e. the focusing plane) and not all the way along the propagation path of the modulated L.A.S.E.R. beam.

By contrast, document US 2010/0133246 proposes using an optical system based on phase and allowing a primary beam to be subdivided into a plurality of secondary beams having different angles of propagation.

The modulation technique according to the invention (by generation of a modulated unique L.A.S.E.R. beam) limits the risks of degradation of the quality of the cut-out surface. In fact, if a portion of the sole modulated L.A.S.E.R. beam is lost along the propagation path of the beam, the intensities of all the impact points of the pattern will be attenuated at the same time (conservation of uniformity between the different impact points of the pattern) but no impact point will disappear in the cutout plane. By contrast with the technique of beam subdivision proposed in US 2010/0133246, if a portion of the plurality of secondary beams is lost along the propagation path, some impact points of the pattern (corresponding to the impact points generated by the lost secondary beams) will be missing from the cutout plane, which substantially degrades the quality of the cut-out performed.

Preferred but non-limiting aspects of the cutting-out apparatus are the following:
  the apparatus may further comprise a control unit of the optical scanner for controlling the displacement of the pattern along a displacement path comprising at least one segment in the cutting-out plane;
  the control unit can be programmed for controlling the activation of the femtosecond laser such that the distance between two adjacent positions of the pattern along a segment of the displacement path being greater than or equal to the diameter of an impact point of the pattern;
  the control unit can be adapted for controlling the displacement of the pattern along a displacement path comprising a plurality of segments, the distance between two adjacent segments of the displacement path being greater than the dimension of the pattern along a perpendicular to the displacement direction of the pattern;
  the control unit can be programmed for controlling the displacement of the pattern along a displacement path comprising a plurality of parallel segments, the distance between two neighboring segments of the displacement path being constant and less than or equal to 3N times the diameter of an impact point, where N corresponds to the number of impact points of the pattern;
  the control unit can be programmed for controlling the displacement of the pattern along a displacement path comprising a plurality of parallel segments, the distance between at least two neighboring segments being different from the distance between at least two other neighboring segments;

the control unit may be able to control the displacement of the pattern along a notch-shaped displacement path in the cutting-out plane;

the control unit may be able to control the displacement of the pattern along a spiral-shaped displacement path in the cutting-out plane;

the sweeping optical scanner may include at least one optical mirror pivoting around at least two axes, the control unit of the optical scanner controlling the pivoting of the mirror so as to displace the pattern along the displacement path;

the apparatus may further comprise at least one Dove prism positioned between the shaping system and the sweeping optical scanner;

the control unit may further be programmed for controlling the activation of the femtosecond laser, the control unit activating the femtosecond laser when the sweeping rate of the optical scanner is greater than a threshold value.

the apparatus can also comprise a filter arranged downstream of the shaping system to block parasite energy generated at the center of the shaping system;

the filter can comprise a plate including: a zone opaque to L.A.S.E.R. radiation arranged at the center of the plate, and a zone transparent to L.A.S.E.R. radiation extending to the periphery of the opaque zone.

the shaping system can consist of a set of phase masks, each mask acting on the phase of the L.A.S.E.R. beam to distribute the energy of the L.A.S.E.R. beam by phase modulation according to a distinct pattern, the masks being fixed to a displacement device, the control unit being programmed for controlling the displacement device (via emission of one or more control signals) so as to shift each mask between:
  an active position in which the mask cuts the optical path of the L.A.S.E.R. beam, and
  an inactive position in which the mask does not extend over the optical path of the L.A.S.E.R. beam;

the shaping system can consist of a spatial light modulator, the control unit being programmed for controlling the spatial light modulator by emission of at least one control signal, each control signal causing display on the spatial light modulator of a phase mask forming a modulation set value;

the control unit can be programmed for controlling the shaping system, said control unit being adapted to send at least first and second control signals (between two respective cutout planes or in the same cutout plane):
  the first control signal causing modulation of the phase of the wave front of the L.A.S.E.R. beam according to a first modulation set value calculated to distribute the energy of the L.A.S.E.R. beam into a plurality of first impact points in the focal plane of the shaping system, the first impact points constituting a first pattern,
  the second control signal causing modulation of the phase of the wave front of the L.A.S.E.R. beam according to a second modulation set value calculated to distribute the energy of the L.A.S.E.R. beam into a plurality of second impact points in the focal plane of the shaping system, the second impact points constituting a second pattern different to the first pattern.

The invention also relates to a control process of apparatus for cutting out human or animal tissue, such as a cornea, or a crystalline, the apparatus including a femtosecond laser capable of sending a L.A.S.E.R. beam in the form of pulses, and a treatment device arranged downstream of the femtosecond laser for processing the L.A.S.E.R. beam generated by the femtosecond laser, the treatment device comprising:

Shaping the L.A.S.E.R. beam to modulate the phase of the wave front of the L.A.S.E.R. beam so as to obtain a single phase-modulated L.A.S.E.R. beam according to a modulation set value calculated to distribute the energy of the L.A.S.E.R. beam in at least two impact points forming the pattern in its focal plane, Focusing the modulated L.A.S.E.R. beam to focus the phase-modulated L.A.S.E.R. beam in a focal plane, Displacement of the pattern in the cutout plane into a plurality of positions.

Preferred, but non-limiting, aspects of the cutting-out apparatus are the following:

the displacement step can consist of displacing the pattern along a displacement path comprising at least a segment in the cutout plane, the process can also comprise an activation step of the femtosecond laser such that the distance between two adjacent positions of the pattern along a segment of the displacement path is greater than or equal to an impact point of the pattern, the displacement step can consist of displacing the pattern along a displacement path comprising a plurality of segments, the distance between two adjacent segments of the displacement path being greater than the dimension of the pattern according to a perpendicular to the displacement direction of the pattern, the displacement step can consist of displacing the pattern along a displacement path comprising a plurality of parallel segments, the distance between two adjacent segments of the displacement path being constant and less than or equal to 3N times the diameter of an impact point, where N corresponds to the number of impact points of the pattern, the displacement step can consist of displacing the pattern along a displacement path comprising a plurality of parallel segments, the distance between at least two adjacent segments being different to the distance between at least two other adjacent segments, the displacement step can consist of displacing the pattern according to a displacement path in the form of a slot in the cutout plane, the displacement step can consist of displacing the pattern according to a displacement path in the form of a spiral in the cutout plane, the process can also comprise an activation step of the femtosecond laser, the control unit activating the femtosecond laser when the scanning speed of the optical scanner is greater than a threshold value, the process can also comprise a filtering step of the L.A.S.E.R. beam to block parasite energy generated at the center of a shaping system, the modulated shaping step can comprise the sub-steps consisting of: modulating the phase of the wave front of the L.A.S.E.R. beam according to a first modulation set value calculated to distribute the energy of the L.A.S.E.R. beam into a plurality of first impact points in the focal plane of the shaping system, the first impact points constituting a first pattern, and to modulate the phase of the wave front of the L.A.S.E.R. beam according to a second modulation set value calculated to distribute the energy of the L.A.S.E.R. beam into a plurality of second impact points in the focal plane of the shaping system, the second impact points constituting a second pattern different to the first pattern, the modulation set value can be a phase mask calculated by using an iterative algorithm based on the Fourier transform.

SHORT DESCRIPTION OF THE DRAWINGS

Other features and advantages of the invention will become clearly apparent from the description which is made hereafter thereof, as an indication and by no means as a limitation, with reference to the appended figures, wherein.

FIGS. 5 to 9, 11 to 18, and 20 to 22, 24 and 28 illustrate different examples of a cut out pattern, FIGS. 10, 19, 23 and 25 to 27 illustrate matrices of cavitation bubbles.

DETAILED DISCUSSION OF THE INVENTION

The invention relates to an apparatus for cutting-out a human tissue by means of a femtosecond laser. In the subsequent description, the invention will be described, as an example, for cutting-out a cornea of a human or animal eye.

1. Cutting-Out Apparatus

Figure 1:
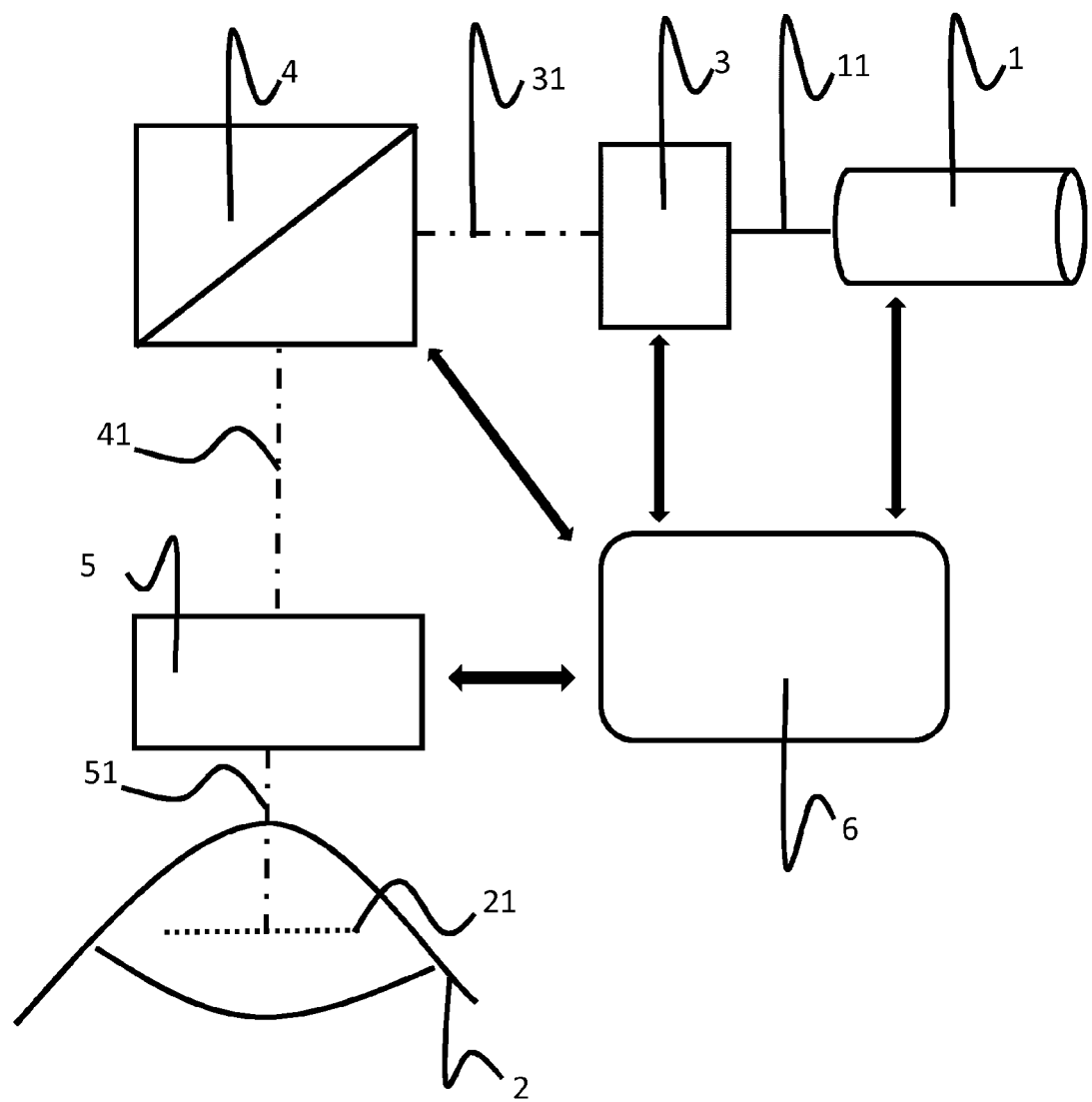
FIG. 1 is a schematic illustration of a circuit including the cutting-out apparatus according to the invention.

With reference to FIG. 1, an embodiment of the cutting-out apparatus according to the invention is illustrated. The latter may be positioned between a femtosecond laser 1 and a target to be treated 2.

The femtosecond laser 1 is able to emit a L.A.S.E.R. beam as pulses. As an example, the laser 1 emits a light with a wavelength of 1,030 nm in the form of pulses of 400 femtoseconds. The laser 1 has a power of 20 W and a frequency of 500 kHz.

The target 2 is for example a human or animal tissue to be cut out such as a cornea or a lens.

The cutting-out apparatus comprises:
a shaping system 3 positioned on the trajectory of the L.A.S.E.R. beam 11 stemming from the femtosecond laser 1,
a sweeping optical scanner 4 downstream from the shaping system 3,
an optical focusing system 5 downstream from the sweeping optical scanner 4.

The cutting-out apparatus also comprises a control unit 6 allowing control of the shaping system 3, the sweeping optical scanner 4 and the optical focusing system 5.

The shaping system 3 allows modulation of the phase of the L.A.S.E.R. beam 11 stemming from the femtosecond laser 1 in order to distribute the energy of the L.A.S.E.R. beam in a plurality of impact points in its focal plane, this plurality of simultaneously generated impact points defining a pattern.

The sweeping optical scanner 4 gives the possibility of orienting the phase-modulated L.A.S.E.R. beam 31 stemming from the shaping system 3 for displacing the cut out pattern along a displacement path predefined by the user in the focusing plane 21.

The optical focusing system 5 allows displacement of the focusing plane 21—corresponding to the cutout plane—of the modulated and deviated L.A.S.E.R. beam 41.

Thus, the shaping system 3 allows simultaneous generation of several impact points defining a pattern, the sweeping optical scanner 4 allows displacement of this pattern in the focusing plane 21, and the optical focusing system 5 allows displacement of the focusing plane 21 in depth so as to generate cut outs in successive planes defining a volume.

The different elements forming the cutting-out apparatus will now be described in more details with reference to the figures.

2. Elements of the Cutting-Out Apparatus 2.1. Shaping System

The spatial shaping system 3 of the L.A.S.E.R. beam gives the possibility of varying the wave surface of the L.A.S.E.R. beam in order to obtain impact points separated from each other in the focal plane. More specifically, the shaping system 3 allows modulation of the phase of the L.A.S.E.R. beam 11 stemming from the femtosecond laser 1 so as to obtain a phase-modulated L.A.S.E.R. single-beam according to a modulation set value calculated to form intensity peaks in the focal plane of the beam, each intensity peak producing a respective impact point in the focal plane corresponding to the cutout plane.

The fact of having a modulated L.A.S.E.R. single-beam makes for easy integration of a sweeping system—such as an optical scanner—for displacing the plurality of secondary L.A.S.E.R. beams in a cutout plane. In fact, since the input diameter of a sweeping system is of the order of the diameter of the initial L.A.S.E.R. beam, the use of a modulated L.A.S.E.R. single-beam (the diameter of which is substantially equal to the diameter of the initial L.A.S.E.R. beam) limits the risks of aberration which can occur with the technique of beam subdivision such as described in US 2010/0133246.

The shaping system 3 is, according to the illustrated embodiment, a spatial light modulator with liquid crystals, known under the acronym of SLM, for "Spatial Light Modulator". The inventors actually found that using an SLM was advantageous despite the basic ideas of the prior art which dissuade the skilled person from using such a device (see especially paragraph [0024] of document US 2015/0164689).

The SLM allows modulation of the final distribution of energy of the L.A.S.E.R. beam, notably in the focal plane 21 corresponding to the cutout plane of the tissue 2. More specifically, the SLM is adapted for modifying the spatial profile of the wave front of the primary L.A.S.E.R. beam 11 stemming from the femtosecond laser 1 for distributing the energy of the L.A.S.E.R. beam in different focusing points in the focusing plane.

This device limits costs associated with modulation of the phase of the wave front and resolves the problems linked to industrialization of the proposed solution. The phase modulation of the wave front may be considered as a two-dimensional interference phenomenon. Each portion of the initial L.A.S.E.R. beam stemming from the source is retarded or advanced relatively to the initial wave front so that each of these portions are redirected so as to produce constructive interference in N distinct points in the focal plane of a lens. This energy redistribution in a plurality of impact points only occurs in a single plane (i.e. the focusing plane) and not at all along the propagation path of the modulated L.A.S.E.R. beam. Thus, the observation of the modulated L.A.S.E.R. beam before or after the focusing plane does not give the possibility of identifying a redistribution of the energy in a plurality of distinct impact points, because of this phenomenon which may be assimilated to constructive interferences (which only take place in a plane and not at all along the propagation like in the case of the separation of an initial L.A.S.E.R. beam in a plurality of secondary L.A.S.E.R. beams).

Figure 2:
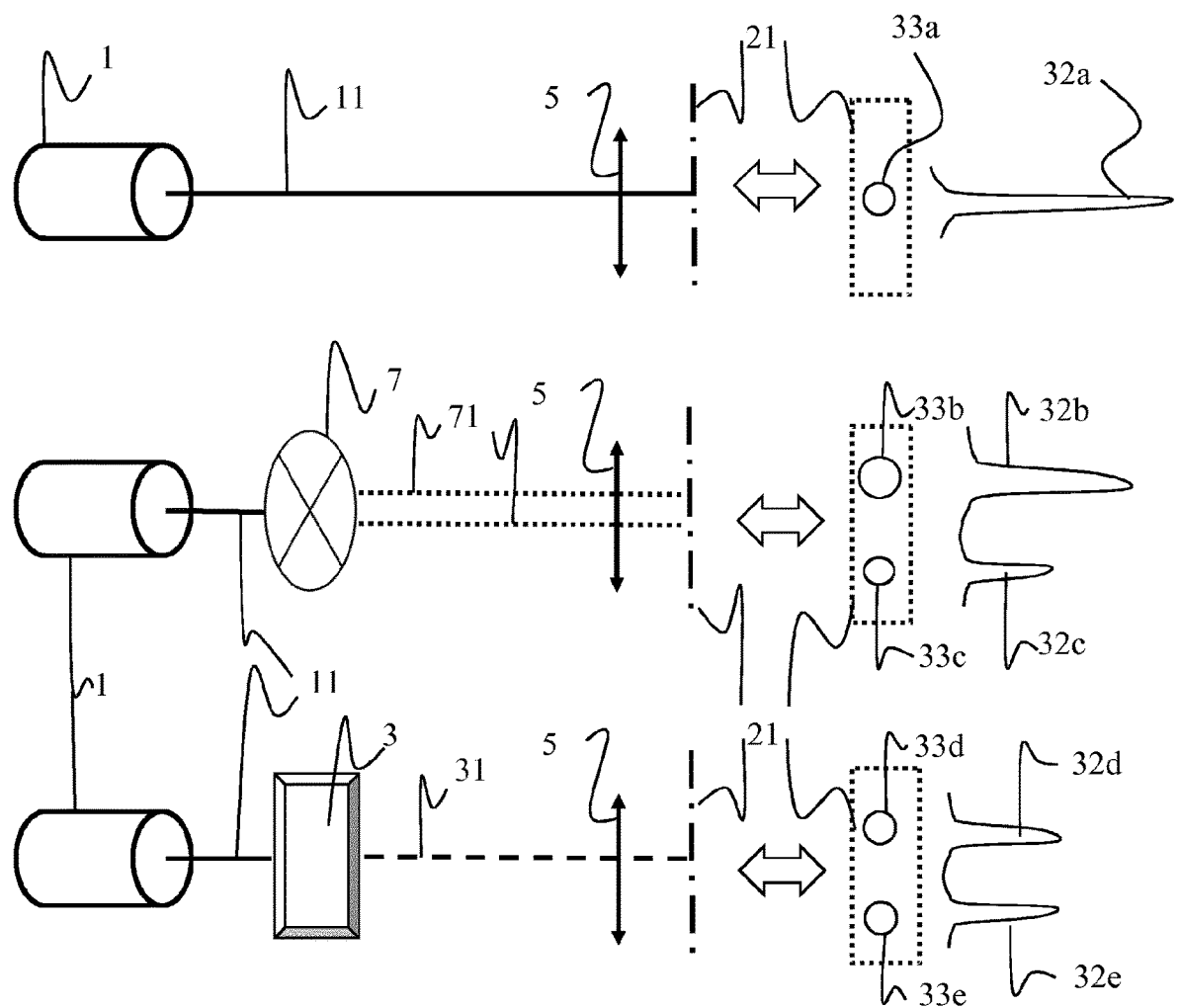
FIG. 2 illustrates an intensity distribution of a L.A.S.E.R. beam in its focal plane.
Figure 3:
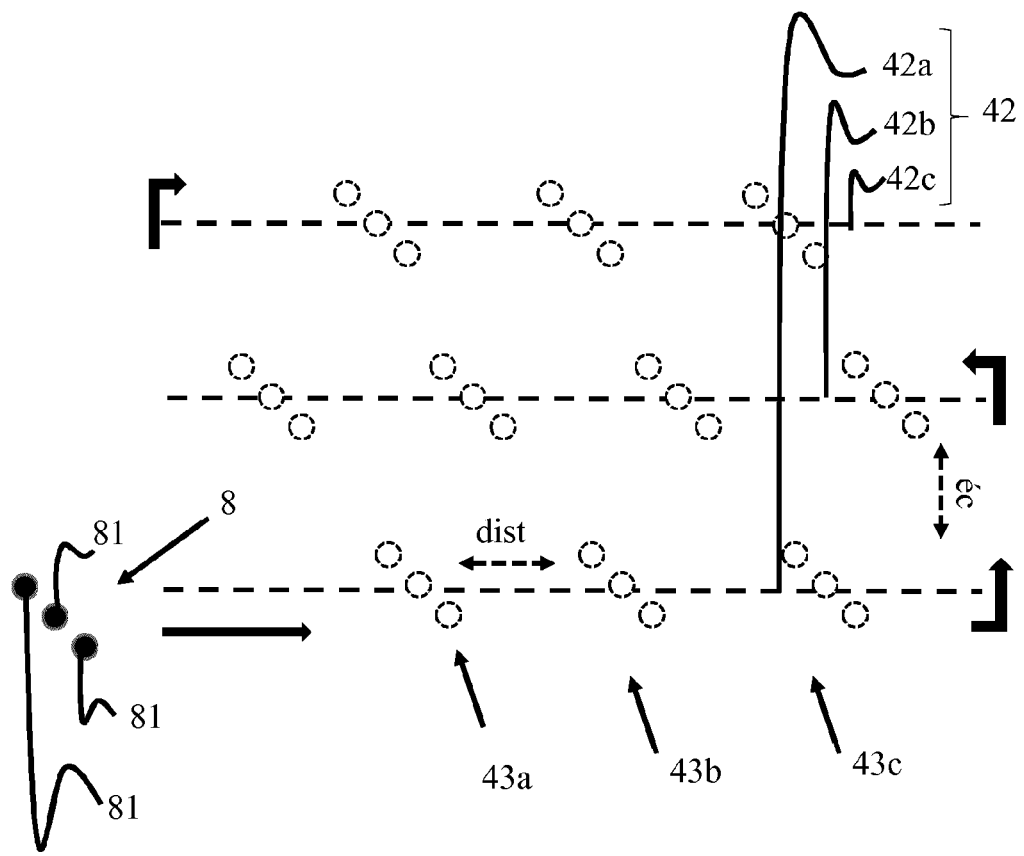
FIG. 3 illustrates a displacement path of a cut out pattern.
Figure 4:
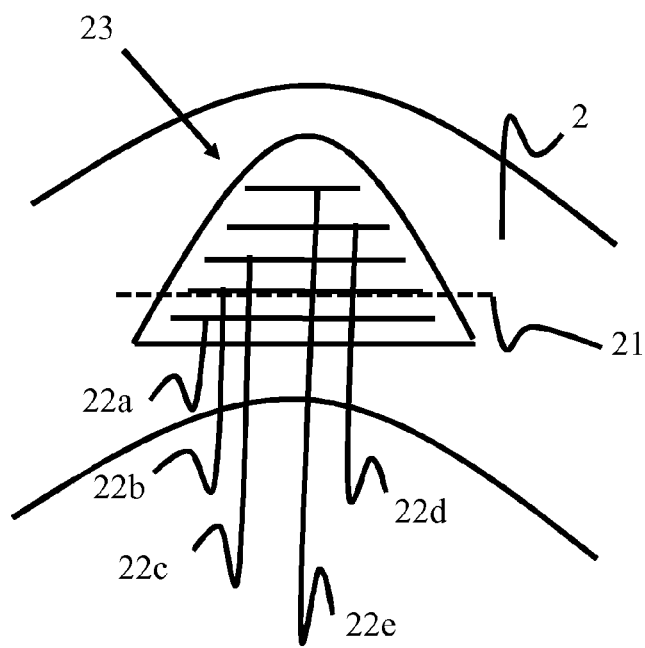
FIG. 4 illustrates planes for cutting-out a volume of tissue to be destroyed.

In order to better understand this phase modulation phenomenon of the wave front, intensity profiles 32a-32e obtained for three examples of distinct optical circuits have been schematically illustrated in FIG. 2. As illustrated in FIG. 2, a L.A.S.E.R. beam 11 emitted by a laser source 1 produces an intensity peak 32a with a Gaussian shape in an impact point 33a in a focusing plane 21. The insertion of a beam splitter 7 between the source 1 and the focusing plane 21 induces the generation of a plurality of secondary L.A.S.E.R. beams 71, each secondary L.A.S.E.R. beam 71 producing a respective impact point 33b, 33c in the focusing plane 21 of the secondary L.A.S.E.R. beams 71. Finally, the insertion between the source 1 and the focusing plane 21 of an SLM 3 programmed by means of a phase mask forming a modulation set value induces modulation of the phase of the wave front of the L.A.S.E.R. beam 11 stemming from the source 1. The L.A.S.E.R. beam 31 for which the phase of the wave front has been modulated gives the possibility of inducing production of several intensity peaks 33d, 33e spatially separated in the focal plane 21 of the L.A.S.E.R. beam, each peak 32d, 32e corresponding to a respective impact point 33d, 33e producing a cut out. The modulation technique of the phase of the wave front gives the possibility of generating several simultaneous cavitation bubbles without any multiplication of the initial L.A.S.E.R. beam produced by the femtosecond laser 1.

The SLM is a device consisting of a layer of liquid crystals with controlled orientation giving the possibility of shaping dynamically the wave front, and therefore the phase of the L.A.S.E.R. beam. The layer of liquid crystals of an SLM is organized like a grid (or matrix) of pixels. The optical thickness of each pixel is electrically controlled by orienting the liquid crystal molecules belonging to the surface corresponding to the pixel. The SLM (9) makes use of the anisotropy principle of liquid crystals, i.e. the modification of the index of the liquid crystals, depending on their spatial orientation. The orientation of liquid crystals may be achieved by means of an electric field. Thus, the modification of the index of the liquid crystals modifies the wave front of the L.A.S.E.R. beam (4).

In a known way, the SLM applies a phase mask, i.e. a map determining how the phase of the beam has to be modified for obtaining a given amplitude distribution in its focusing plane. The phase mask is a two—dimensional image, each point of which is associated with a respective pixel of the SLM. This phase mask gives the possibility of controlling the index of each liquid crystal of the SLM by converting the value associated with each point of the mask — illustrated in gray levels comprised between 0 and 255 (therefore from black to white) — into a control value— represented in a phase comprised between 0 and 2n. Thus, the phase mask is a modulation set value displayed on the SLM for causing by reflection an uneven spatial phase shift of the L.A.S.E.R. beam (4) illuminating the SLM. Of course, one skilled in the art will appreciate that the gray level range may vary depending on the SLM version used. For example in certain cases, the gray level range may be comprised between 0 and 220. The phase mask is generally calculated by:

an iterative algorithm based on the Fourier transform, such as an algorithm of "IFTA" type, acronym for "Iterative Fourier Transform Algorithm", or by - diverse optimization algorithms, such as genetic algorithms, or simulated annealing.

This allows controlling the homogeneity, the intensity, the quality and the form of the different impact points generated in the cutout plane.

Different phase masks may be applied to the SLM depending on the number and on the position of the impact points desired in the focal plane of the L.A.S.E.R. beam. In every case, one skilled in the art knows how to calculate a value in each point of the phase mask in order to distribute the energy of the L.A.S.E.R. beam in different focusing spots in the focal plane.

The SLM therefore gives the possibility, from a Gaussian L.A.S.E.R. beam generating a single impact point, and by means of the phase mask, of distributing its energy by phase modulation so as to simultaneously generate several impact points in its focusing plane from a single L.A.S.E.R. beam shaped by phase modulation (a single beam upstream and downstream from the SLM).

In addition to a reduction in the time for cutting-out the cornea, the phase modulation technique of the L.A.S.E.R. beam according to the invention allows other improvements, such as a better surface quality after cutting-out or reducing the endothelial mortality. The different impact points of the pattern may for example be regularly spaced out over the two dimensions of the focal plane of the L.A.S.E.R. beam, so as to form a grid of L.A.S.E.R. spots.

Thus, the shaping system 3 gives the possibility of carrying out a surgical cutting-out operation in a rapid and efficient way. The SLM gives the possibility of shaping dynamically the wave front of the L.A.S.E.R. beam, since it may be parameterized digitally. This modulation allows shaping of the L.A.S.E.R. beam in a dynamic and reconfigurable way.

The SLM may be configured for shaping the wave front of the L.A.S.E.R. beam in any other way. For example, each impact point may have any geometrical shape, other than circular (for example an ellipse, etc.). This may have certain advantages depending on the considered application, such as an increase in the speed and/or the quality of the cut out.

2.2. Sweeping Optical Scanner

The sweeping optical scanner 4 allows deviation of the phase modulated L.A.S.E.R. beam 31 so as to displace the pattern 8 in a plurality of positions 43a-43c in the focusing plane 21 corresponding to the cutout plane.

The sweeping optical scanner 4 comprises:
  an input orifice for receiving the phase-modulated L.A.S.E.R. beam 31 stemming from the shaping unit 3,
  one (or several) optical mirror(s) pivoting around at least two axes for deviating the phase-modulated L.A.S.E.R. beam 31, and
  an output orifice for sending the deviated modulated L.A.S.E.R. beam 41 towards the optical focusing system 5.

The optical scanner 4 used is for example a sweeping head IntelliScan III from SCANLAB AG.

The input and output orifices of such an optical scanner 4 have a diameter of the order of 10 to 20 millimeters, and the sweeping rates which may be attained are of the order of 1 m/s to 10 m/s.

The mirror(s) is (are) connected to motor(s) in order to allow their pivoting. These motor(s) for the pivoting of the mirror(s) is (are) advantageously controlled by the unit of the control unit 6 which will be described in more details subsequently.

The control unit 6 is programmed for controlling the sweeping optical scanner 4 so as to displace the pattern 8 along a displacement path 42 contained in the focusing plane 21. In certain embodiments, the displacement path 42 comprises a plurality of cutting-out segments 42a-42c. The displacement path 42 may advantageously have a niche shape. In this case, if the optical scanner 4 begins with a first cutting-out segment 42a on the left, it will begin with the second cutting-out segment 42b on the right, and then the third cutting-out segment 42c on the left, and then the next segment on the right, and so forth over the whole displacement path 42 of the pattern 8. This will give the possibility of accelerating the cutting-out of the tissue while avoiding the requirement for the optical scanner 4 of repositioning the pattern 8 at the beginning of each successive cutting-out segment 42a-42c.

In order to further accelerate the cutting-out operation in the focusing plane 21, the displacement path 42 may advantageously have a spiral shape. This gives the possibility of maintaining constant the sweeping rate of the optical scanner 4 in the whole cutout plane. Indeed, in the case of a displacement path 42 with the shape of a niche, the optical scanner 4 has to stop at the end of each cutting-out segment 42a for moving on to the next cutting-out segment 42b, which consumes time.

The sweeping of the beam has an influence on the result of the obtained cut out. Indeed, the sweeping rate used, as well as the pitch of the sweeping are parameters which influence the quality of the cut out.

Preferably, the sweeping pitch—corresponding to the distance "dist" between two adjacent positions 43a, 43b of the pattern 8 along a segment of the displacement path 42—is selected to be greater than or equal to the diameter of an impact point 81 of the pattern 8. This gives the possibility of limiting the risks of superposing impact points during successive shots.

Also, when the displacement path 42 has a niche shape, the distance "ec" between two adjacent segments 42a, 42b of the displacement path 42 is preferably selected to be greater than the size of the pattern 8 along a perpendicular to its displacement direction. This also gives the possibility of limiting the risk of superposition of the impact points 81 during successive shots.

Finally, for limiting the duration of the cutting-out operation in the cutting-out plane, while guaranteeing a certain quality of the cutting-out, the distance between two adjacent segment 42a, 42b of the displacement path 42 may be selected to be equal to a maximum (and preferably less than) of 3N times the diameter of an impact point 81, wherein N is the number of impact points of the pattern 8.

In an embodiment, the cutting-out apparatus further comprises a Dove prism. The latter is advantageously positioned between the shaping system 3 and the sweeping optical scanner 4. The Dove prism gives the possibility of applying a rotation of the pattern 8 which may be useful in certain applications or for limiting the size of the area for initiating each cut-out segment 42a-42c.

Advantageously, the control unit 6 may be programmed for activating the femtosecond laser 1 when the sweeping rate of the optical scanner 4 is greater than a threshold value.

This gives the possibility of synchronizing the emission of the L.A.S.E.R. beam 11 with the sweeping of the sweeping optical scanner 4. More specifically, the control unit 6 activates the femtosecond laser 1 when the pivoting rate of the mirror(s) of the optical scanner 4 is constant. This gives the possibility of improving the quality of the cutting-out for producing a homogenous surfacing of the cutting-out plane.

2.3 Optical Focusing System

The optical focusing system 5 gives the possibility of displacing the focusing plane 21 of the modulated and deviated L.A.S.E.R. beam 41 in a plane for cutting-out the tissue 2, desired by the user.

The optical focusing system 5 comprises:
- an input orifice for receiving the phase-modulated and deviated L.A.S.E.R. beam from the sweeping optical scanner,
- one (or several) motor-driven lens(es) for allowing its (their) displacement in translation along the optical path of the phase-modulated and deviated L.A.S.E.R. beam, and
- an output orifice for sending the focused L.A.S.E.R. beam towards the tissue to be treated.

The lens(es) used with the optical focusing system 5 may be f-theta lenses or telecentric lenses. With f-theta and telecentric lenses, it is possible to obtain a focusing plane over the whole field XY, unlike standard lenses for which it is curved. This gives the possibility of guaranteeing a constant focused beam size over the whole field. For f-theta lenses, the position of the beam is directly proportional to the angle applied by the scanner while the beam is always normal to the sample for telecentric lenses.

The control unit 6 is programmed for controlling the displacement of the lens(es) of the optical focusing system 5 along an optical path of the L.A.S.E.R. beam so as to displace the focusing plane 21 in at least three respective cutting-out planes 22a-22e so as to form a stack of cutting-out planes of the tissue 2. This gives the possibility of performing a cut-out in a volume 23, for example within the scope of refractive surgery.

The control unit 6 is able to control the displacement of the optical focusing system 5 in order to displace the focusing plane 21 between a first extreme position 22a and a second extreme position 22e, in this order. Advantageously, the second extreme position 22e is closer to the femtosecond laser 1 than the first extreme position 22a.

Thus, the cutting-out planes 22a-22e are formed by beginning with the deepest cutout plane 22a in the tissue and by stacking the successive cutout planes up to the most superficial cutout plane 22e in the tissue 2. Problems associated with the penetration of the L.A.S.E.R. beam into the tissue 2 are thereby avoided. Indeed, the cavitation bubbles form an opaque barrier of bubbles (known under the name of "OBL", an acronym for "Opaque Bubble Layer") preventing propagation of the energy from the L.A.S.E.R. beam under the latter. It is therefore preferable to begin by generating the deepest cavitation bubbles in priority in order to improve the efficiency of the cutting-out apparatus.

Preferably, the length of the optical path between the shaping system 3 and the optical focusing system 5 is less than 2 meters, and even more preferentially less than 1 meter. This gives the possibility of limiting the power losses due to the energy dispersed over the optical path. Indeed, the larger the distance between the shaping system 3 and the optical focusing system 5, the larger is the power loss over the path.

Advantageously, the control unit 6 may be programmed for varying the shape of the pattern 8 between two successive cutout planes 22a-22b (or 22b-22c, or 22c-22d, or 22d-22e). Indeed, during the cutting-out in a volume 23, it may be preferable to increase the accuracy of the cutting-out in the peripheral cutout planes 22a, 22e and to increase the cutting-out rate in the intermediate cutout planes 22b, 22c, 22d located between the peripheral cutout planes 22a, 22e. For example, in the case of the cutting-out of a volume 23 consisting of a stack of five cutout planes 22a-22e, the control unit 6 may control the shaping system 3 by transmitting to it:

a first phase mask corresponding to a first pattern allowing an increase in the accuracy of the cutting-out when the focusing plane corresponds to the first and second cutout planes 22a and 22e, a second phase mask when the focusing plane corresponds to the second, third and fourth cutout planes 22b-22d.

Also, the control unit 6 may be programmed for varying the pitch "dist" of the sweeping optical scanner 4 and/or the shape of the cut-out area (by modifying the displacement path of the pattern) between two respective cutout planes. This also gives the possibility either of increasing the accuracy of the cutting-out, or the cutting-out rate in one cutout plane to another.

Finally, the control unit 6 may be programmed for controlling the sweeping optical scanner 4 so as to vary the area cut out in the focusing plane 21 between two successive cutout planes 22d, 22e. This gives the possibility of varying the shape of the finally cut-out volume 23 depending on the targeted application.

Preferably, the distance between two successive cutout planes is comprised between 2 µm and 500 µm, and notably:

between 2 and 20 µm for treating a volume requiring great accuracy, for example in refractive surgery, with preferably a spacing comprised between 5 and 10 µm, or between 20 and 500 µm for treating a volume not requiring great accuracy, such as for example for destroying the central portion of a lens core, with preferably a spacing comprised between 50 and 200 µm.

Of course, this distance may vary in a volume 23 consisting of a stack of cutout planes 22a-22e.

2.4 Filter

The cutting-out apparatus can also comprise a filter arranged downstream of the shaping system 3.

On the one hand the filter blocks the "parasite" energy generated at the center of the shaping system 3 (phenomenon known as "zero order"). In fact, during the phase modulation of the L.A.S.E.R. beam with the shaping system, part of the L.A.S.E.R. beam originating from the laser source 1 is not modulated (because of the space existing between the pixels of the liquid crystals of the SLM). This part of the non-modulated L.A.S.E.R. beam can cause generation of an energy peak forming at the center of the SLM.

The filter also limits the risk of L.A.S.E.R. lesions unexpected for the patient in the event of malfunction of the shaping system 3. In fact, if the shaping system 3 is defective, the L.A.S.E.R. beam is not modulated, which causes formation of a high-energy peak at the center of the shaping system 3. By blocking this high-energy peak, the filter prevents unintentional generation of cavitation bubbles.

The filter can be placed between two converging lenses arranged downstream of the shaping system 3. In fact, the order 0 can be eliminated in a Fourier plane only (that is, in the focal point of a lens), where shaping of the beam takes place.

The filter consists for example of a plate transparent to L.A.S.E.R. radiation over its entire surface with the exception of a central region of the plate which is opaque to L.A.S.E.R. radiation. To make the central region of the plate opaque to L.A.S.E.R. radiation, the filter can comprise an opaque lozenge arranged at the center of the surface, the lozenge having a diameter greater than or equal to the diameter of a L.A.S.E.R. beam.

This filter is then positioned such that a straight line normal to the shaping system 3, and passing through the center of said shaping system 3 also passes through the central region opaque to L.A.S.E.R. radiation.

2.5 Control Unit

As indicated earlier, the control unit 6 gives the possibility of controlling the different elements making up the cutting-out apparatus, i.e. the femtosecond laser 1, the shaping system 3, the sweeping optical scanner 4 and the optical focusing system 5.

The control unit 6 is connected to these different elements via one (or several) communication bus(es) giving the possibility:

of transmitting control signals such as
the phase mask to the shaping system,
the activation signal to the femtosecond laser,
the sweeping rate to the sweeping optical scanner,
the position of the sweeping optical scanner along the displacement path,
the cutting-out depth to the optical focusing system.

receiving measurement data from the different elements of the system such as
the sweeping rate attained by the optical scanner, or
the position of the optical focusing system, etc.

The control unit 6 may consists of one (or several) work station(s) and/or one (or several) computer(s) or may be of any other type known to one skilled in the art. The control unit 6 may for example comprise a portable telephone, an electronic tablet (such as an IPAD®), a personal digital assistant (or "PDA", an acronym of the expression "Personal Digital Assistant"), etc. In every case, the control unit 6 comprises a processor programmed in order to allow control of the femtosecond laser 1, of the shaping system 3, of the sweeping optical scanner 4, of the optical focusing system 5, etc.

2.6 Pattern

The reconfigurable modulation of the wave front of the L.A.S.E.R. beam gives the possibility of generating multiple simultaneous impact points 81 each having a size and a control position in the focusing plane 21.

These different impact points 81 form a pattern 8 in the focal plane 21 of the modulated L.A.S.E.R. beam.

The number of impact points 81 of the pattern 8 decreases as many times as the time required for the surgical cutting-out operation.

However, the size of the pattern 8, the number of impact points 81 which it comprises and their respective positions relatively to the displacement direction are technical features cleverly selected for meeting technical constraints associated with the cutting-out of tissue, as this will emerge subsequently.

2.6.1. Constraints and Selected Solutions 2.6.1.1. Maximum Number of Impact Points Per Pattern In order to accelerate the cutting-out of the tissue 2, it is preferable to have a pattern 8 including a maximum number of impact points 81. In present ophthalmic laser systems, the energy per pulse and per spot required for corneal cutting-out is of the order of 1 µJ. Thus, with a femtosecond laser—such as a laser source Satsuma (marketed by Amplitude Système)—providing a power of 20 W at a rate of 500 kHz, i.e. at most an energy of 40 µJ/pulse, it is theoretically possible to generate a pattern 8 consisting of 40 identical impact points 81.

However, in any laser system, losses occur along the optical trajectory. Thus, in a prototype tested by the Applicant, the power arriving on the cornea was only 12 W at most for a shaping of six impact points 81 of a global size (30 µm*22 µm). The diameter of the focus beam was a diameter of 8 µm, versus about 4 µm at most for present ophthalmic lasers. Within the scope of a prototype tested by the Applicant, a 4 times greater energy per spot was required as compared with present ophthalmic lasers, i.e. 4 µJ. Thus for this prototype, the use of a pattern consisting of six impact points 81 (at the most) was selected. Of course, if the power of the femtosecond laser 1 is greater, the pattern 8 may comprise a number of impact points 81 greater than six.

2.6.1.2. Distribution of the Impact Points in the Pattern

The six impact points 81 of the pattern 8 may be distributed according to different configurations.

For example the six impact points 81 may be distributed along a single line. The total length of the pattern 8 is then equal to the sum between the diameter of an impact point 81 and the center-to-center distance between the extreme impact points 81 of the pattern 8. The width of the pattern 8, as for it, is equal to the diameter of an impact point 81.

As indicated earlier, the shaping of the L.A.S.E.R. beam causes a power loss, due to the energy dispersed over the optical path. The global size of the shaping (and therefore the size of the pattern 8) is part of the factors having an influence on this energy loss.

The greater the size (in length or in width) of the pattern 8, the greater is the power loss. A distribution of six impact points 81 on a single line therefore induces a significant power loss.

As an indication:
a pattern 8 with a size of 30 µm*22 µm comprising six impact points 81 causes a power loss of about 10%, while
a pattern 8 with a size of 84 µm*20 µm comprising five impact points 81 causes a power loss of about 25%.

Thus, for a given number of impact points 81, "compacts" patterns (ratio of the sizes in length and in width close to 1) cause a lower energy loss.

This is why the impact points 81 of the pattern 8 are preferably comprised in a surface for which the ratio between the length and the width is comprised between 1 and 4, preferentially between 1 and 2, and even more preferentially between 1 and 1.5.

For example, the six impact points 81a-81f of the pattern may be distributed over first and second parallel lines 82, 83:
the first line 82 passing through three impact points 81a-81c form a first triplet, and
the second line 83 passing through three other impact points 81d-81f forming a second triplet distinct from the first triplet.

Figure 5:
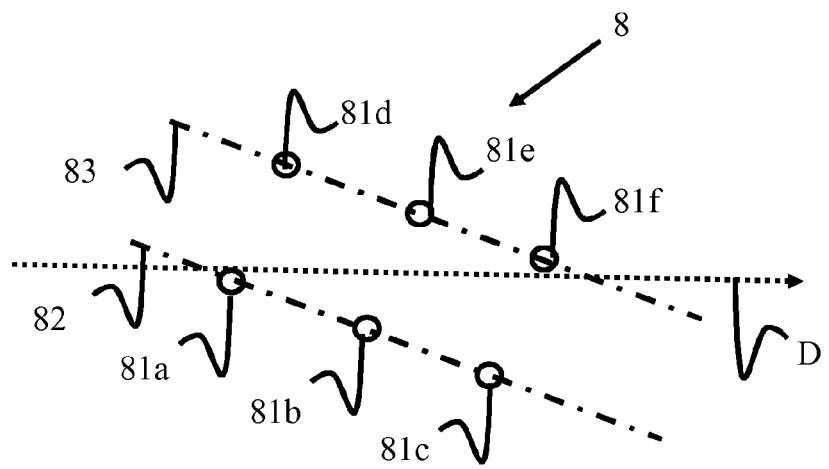

A pattern corresponding to this distribution is illustrated in FIG. 5. Advantageously, the impact points 81a-81f of the pattern may be shifted from one line to the other along the displacement direction D. More specifically, the impact points 81a-81c of the first triplet may be shifted by a non-zero distance (along the displacement direction D) relatively to the impact points 81d-81f of the second triplet. This gives the possibility of avoiding superposition of cavitation bubbles in the cutout plane during the displacement of the pattern 8 by the sweeping optical scanner 4.

2.6.1.3. Minimum Distance Between Impact Points of the Pattern

In addition to the distribution of the impact points 81 of the pattern 8, another parameter of the pattern relates to the distance between the adjacent impact points.

This distance is defined by constraints related to the shaping system.

During the shaping operation of the L.A.S.E.R. beam stemming from the femtosecond laser, "too close" impact points interfere with each other because of the spatial coherence of the source. These interferences degrade the shape of the impact points and make it impossible to control the laser intensity level on each impact point. It is therefore preferable that the distance between these adjacent impact points of the pattern be sufficient in order to limit this interference phenomenon between too close impact points.

This "sufficient distance" depends on the focusing of the beam. The more the beam will be focused, the smaller will be this distance. Conversely, the less focused will be the beam, the larger will be this distance.

By taking into account the constraints of working distance related to the surgical applications of the anterior segment of the eye, of the reproducibility of the shaping as well as of the aberrations of the optical system degrading the spatial coherence of the beam, the separation limit of two spots is located at about 10 µm.

This is why the "sufficient distance" from center-to-center between two adjacent impact points is greater than 5 µm, preferentially greater than 10 µm and even more preferentially comprised between 10 µm and 20 µm, notably between 10 µm and 15 µm.

2.6.1.4. Orientation of the Pattern Relatively to the Displacement Direction

The basic form illustrated in FIG. 5 may be oriented in different ways in the lattice.

Figure 6:
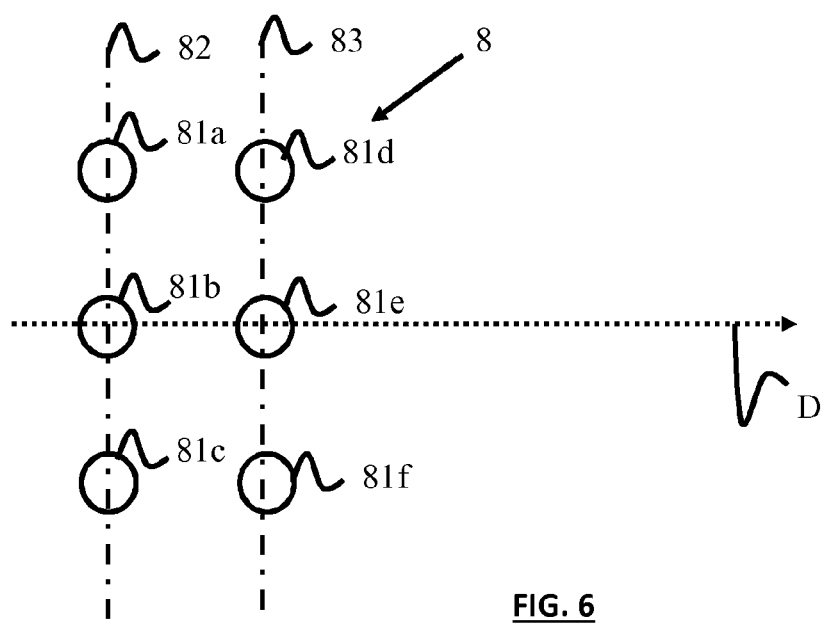

The most obvious orientation of this basic form for one skilled in the art is illustrated in FIG. 6. This orientation consists of displacing the pattern along a displacement direction D perpendicular to both lines 82, 83 defined by the first and second triplets of impact points 81a-81c and 81d-81f.

However, several limitations related to the shaping system and to the displacement direction of the pattern prevent the use of such an orientation.

As described earlier, the distance between two adjacent impact points 81a, 81b of the pattern is preferentially greater than 10 µm. By displacing the pattern along a displacement direction perpendicular to both lines 82, 83 defined by the first and second triplets of impact points 81a-81c, 81d-81f, the distance between the cavitation bubbles generated on adjacent segments 42a, 42b, parallel to the displacement direction of the pattern will be of the order of 15 µm.

Now, a "conventional" distance between adjacent cavitation bubbles for the cutting-out of a cornea is of the order of 2 µm to 7 µm, notably equal to 5 µm.

Therefore it is necessary to "tilt" the pattern 8 so that the neighboring cavitation bubbles generated on adjacent segments 42a, 42b parallel to the displacement direction D of the pattern 8 are spaced apart by a distance substantially equal to 5 µm in the displacement direction.

It will be noted that on a same segment 42a, the 5 µm distance between two adjacent cavitation bubbles may be obtained by adjusting the displacement pitch of the sweeping optical scanner 4.

2.6.2. Examples of Retained Patterns

Figure 7:
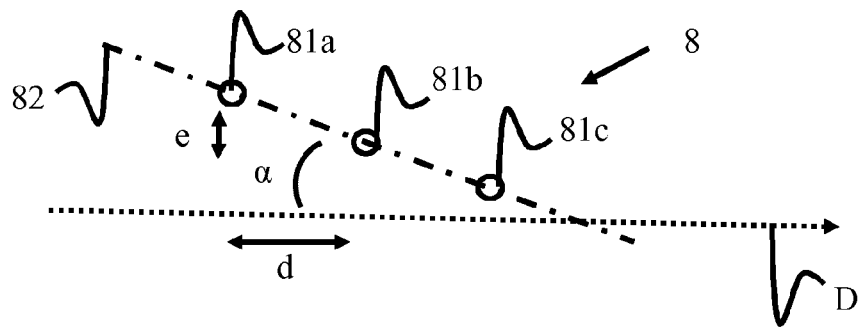
Figure 8:
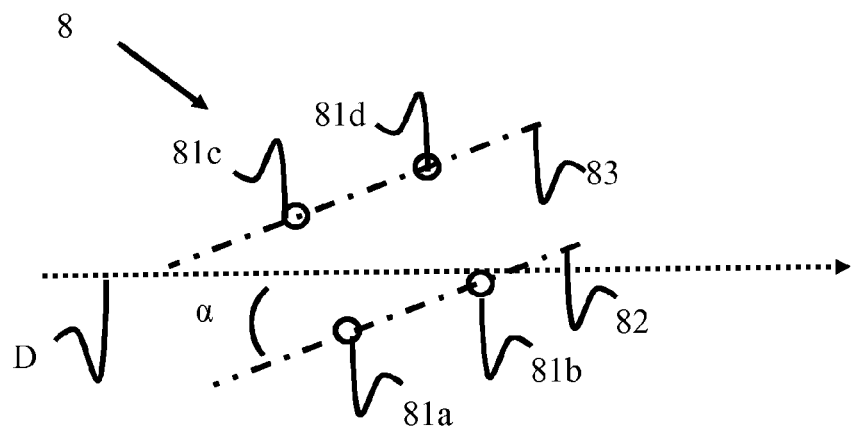
Figure 9:
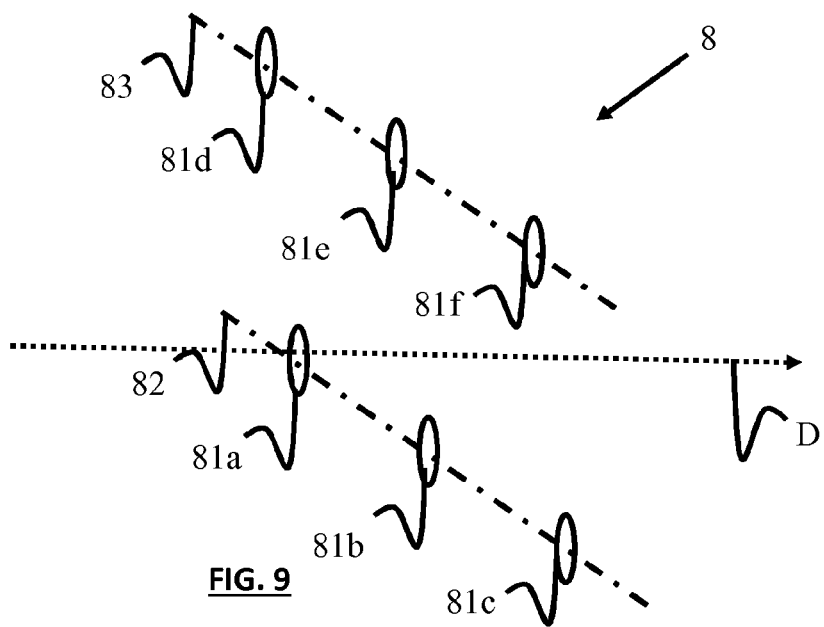

With reference to FIGS. 7 to 9, different examples of patterns which may be used with the cutting-out apparatus according to the invention are illustrated.

In the embodiment illustrated in FIG. 7, the pattern comprises three impact points 81a-81c extending along a line 82 of the pattern 8. The impact points are spaced apart by a distance "d" along the displacement direction D. The line of the pattern is tilted by an angle "a" relatively to the displacement direction D of the sweeping optical scanner 4 so that the cavitation bubbles along a straight line perpendicular to the displacement direction D are spaced apart by a distance "e" in the cutout plane. One then has the following relationship between the different distances "d" and "e", and the tilt angle "a":

$$\alpha = \tan^{-1}\left(\frac{e}{d}\right)$$

Preferably, the tilt angle "a" of the pattern is comprised between 10° and 80°.

In the embodiment illustrated in FIG. 8, the pattern comprises four impact points 81a-81d extending along two parallel lines 82, 83 of the pattern 8:
  A first pair of impact points 81a, 81b extends along a first line 82 of the pattern,
  A second pair of impact points 81c, 81d extends along a second line 83 of the pattern.

This pattern present has a square shape tilted with a tilt angle "a" relatively to the displacement direction of the sweeping optical scanner. One has the following relationship:

$$\alpha = \tan^{-1}\left(\frac{e}{d}\right)$$

With:
  "a" being the tilt angle of each line of the pattern relatively to the displacement direction,
  "d" corresponding to the distance between two adjacent impact points, and
  "e" corresponding to the distance between two adjacent impact points along a direction perpendicular to the displacement direction of the pattern.

In the embodiment illustrated in FIG. 9, the pattern comprises six impact points 81a-81f extending along two parallel lines of the pattern 8:
  A first triplet of impact points extends along a first line of the pattern,
  A second triplet of impact points extends along a second line of the pattern.

This pattern has a rectangular shape tilted with a tilt angle "a" relatively to the displacement direction of the sweeping optical scanner. One has the following relationship:

$$\alpha = \tan^{-1}\left(\frac{e}{d}\right)$$

With:
  "a" being the tilt angle of each line of the pattern relatively to the displacement direction,
  "d" corresponding to the distance between two adjacent impact points, and "e" corresponding to the distance between two adjacent impact points along a direction perpendicular to the displacement direction of the pattern.

2.6.3. Theory Relative to the Determination of Patterns

In the following, an approach applied by the Applicant will be described for determining the possible shapes of the patterns of impact points giving the possibility of finally obtaining an arrangement of cavitation bubbles consisting of a repetitive regular matrix:
  either a square matrix,
  or an equilateral triangle matrix,
while observing the minimum spacing between adjacent impact points for limiting the interference phenomenon described earlier.

There exists a variety of possible patterns for obtaining by projection during their displacement, a homogeneous and repetitive matrix of cavitation bubbles distant from each other by 5 μm, over the whole treated surface. But there also exists an "ideal" matrix, for which the impact points are sufficiently far from each other for avoiding interferences, and sufficiently close so that the total surface of the pattern is small and is included in a restricted field, which is preferable because of the limited size of the optics and of the mirrors which are found on the path of the L.A.S.E.R. beam.

We simply proceeded with the observation of an arrangement of spots, either with a square matrix or with an equilateral triangle matrix, and we determine the possible patterns for obtaining this arrangement, once the pattern is set into motion by the sweeping optical scanner.

Figure 10:
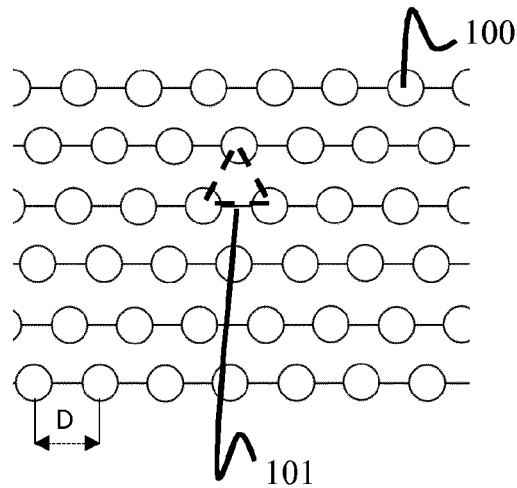

2.6.3.1. Searching for a Pattern in Order to Obtain an Arrangement of Cavitation Bubbles as an Equilateral Triangle Matrix In FIG. 10 illustrating a cut out plane including a plurality of cavitation bubbles 100, an arrangement of bubbles as an equilateral triangle forming a matrix 101 may be observed.

Figure 11A:
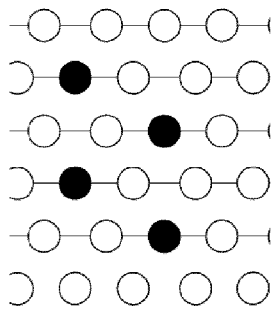
Figure 11B:
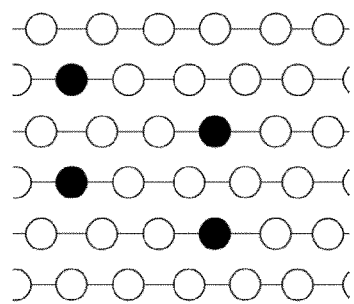
Figure 11C:
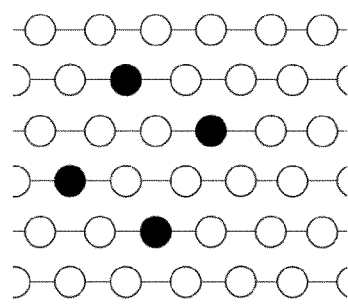
Figure 12:
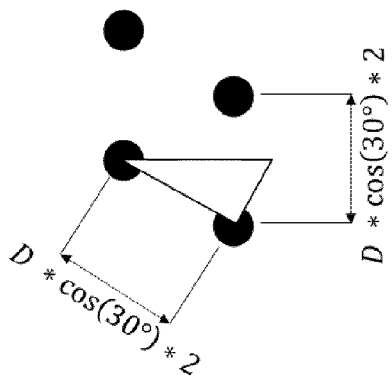
Figure 12:
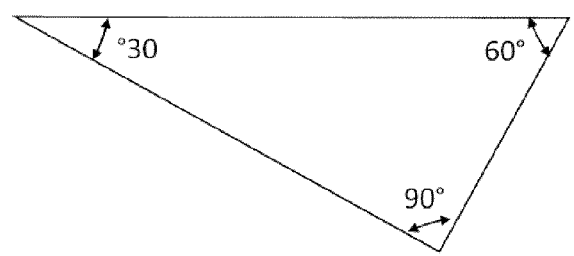

The observation, leads us to identify several possible patterns, which are included in this matrix, as illustrated in FIGS. 11a to 11c.

In practice, none of the three matrices shown above may be used. Indeed, if the distance separating 2 bubbles of the cut out surface is D, or 5 μm, in order to avoid interferences the minimum distance between 2 impact points of the pattern also has to be equal to 10 μm, i.e. at least 2D.

Now, in the three examples of patterns illustrated in FIGS. 11a to 11c, there is always at least two impact points of the pattern too close to each other (distance=D*(Cos(30°)*2)=1.73*D. I.e. for D=5 μm, one has a distance of 8.65 μm (cf. FIG. 12).

These observations therefore lead us to define a pattern for which all the impact points are at least distant from each other by 2*D and which gives the possibility of obtaining the arrangement as an equilateral triangle pattern.

A first pattern example is illustrated in FIGS. 13 to 15, wherein all the points are distant from each other at least by 2*D, i.e. for the distances A and B if D=5 μm:

$$A = D * \cos(30°) * 4 = 17 \text{ μm}$$

$$B = \sqrt{(2.5D)^2 + (\cos(30°)*D)^2} = 13.22 \text{ μm}$$

On the other hand, the distance between the most spaced apart two points of the matrix is $$C = \sqrt{(4.5D)^2 + (\cos(30°)*5D)^2} = 31.22 \text{ μm}$$

Finally, in this matrix, accurate angulation (cf. FIG. 15) gives the possibility of reproducing the regular pattern as an equilateral triangle, and the angles relatively to the horizontal and to the vertical are:

$$A = D \times \cos(30°) \times 4$$

$$B = \sqrt{(2.5D)^2 + [(\cos(30°) \times D)]^2}$$

$$C = \sqrt{(4.5D)^2 + [\cos(30°) \times 5D)]^2}$$

α=19.1°

β=16.1°

Figure 16:
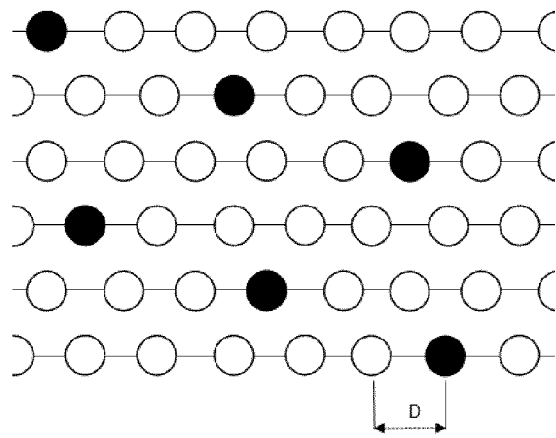
Figure 17:
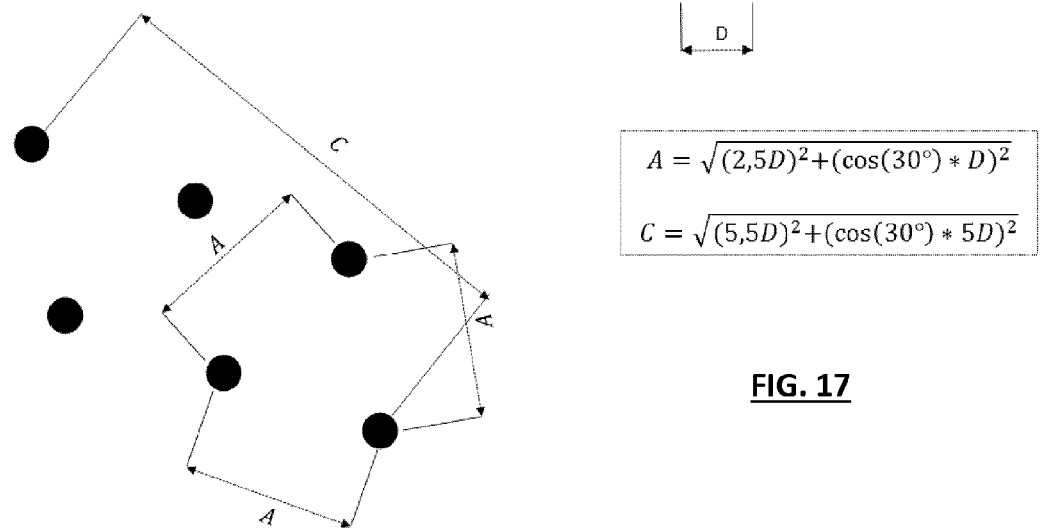
Figure 18:
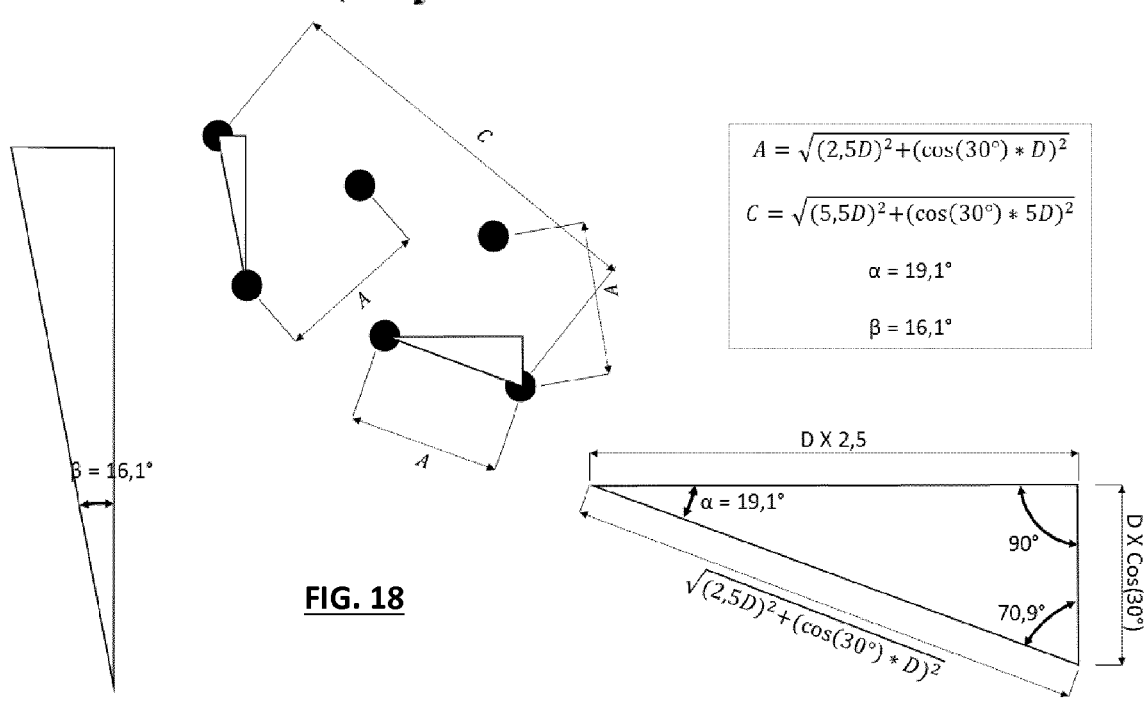

A second example of a pattern is illustrated in FIGS. 16 to 18, wherein all the points are distant from each other by at least 2*D, i.e. for the distances A if D=5 μm:

$$A=\sqrt{(2.5D)^2+(\cos(30°)*D)^2}=13.22 \text{ μm}$$

On the other hand, the distance between the two most spaced apart points of the matrix is $$C=\sqrt{(5.5D)^2+(\cos(30°)*5D)^2}=35 \text{ μm}$$

Finally, in this pattern, accurate angulation gives the possibility of reproducing the equilateral triangle matrix, and the angles relatively to the horizontal and to the vertical are:

$$A=\sqrt{(2.5D)^2+[(\cos(30°)\times D)]^2}$$

$$C=\sqrt{(5.5D)^2+[(\cos(30°)\times 5D)]^2}$$

α=19.1°

β=16.1°

From the foregoing, we have just demonstrated that two different patterns may be used for obtaining after setting into motion, an arrangement of regular bubbles positioned according to a matrix as an equilateral triangle.

The selection between the first or the second pattern would rather be in favor of the first, since the maximum spacing between the most distant 2 points is 31.22 μm instead of 35 μm, therefore a more compact shape.

Another benefit of these patterns, is that the number of points may be increased to more than 6 (2×3 points) by adding new rows of points, by observing the same distances and angulations and by passing to patterns of 9 (3×3) or 12 points (3×4) or more.

2.6.3.2. Searching for a Pattern in Order to Obtain a Cavitation Bubble Arrangement as a Square Matrix In FIG. 19, illustrating a cut out plane including a plurality of cavitation bubbles 100, a square arrangement of bubbles forming a matrix 101 may be observed.

The observation leads up to identifying a possible pattern, which is included in this matrix, and which observes the minimum spacing between 2 points equal to twice the distance D:

$$A=\sqrt{8D^2}=14.14 \text{ μm}$$

$$B=\sqrt{5D^2}=11.18 \text{ μm}$$

$$E=3D=15 \text{ μm.}$$

On the other hand, the distance between the two most spaced apart points of the pattern is:

$$C=\sqrt{41D^2}=32 \text{ μm}$$

Finally, in this matrix, accurate angulation gives the possibility of reproducing the regular pattern as a square, and the angle relatively to the horizontal is α=26.56.

2.6.3.3. Particular Case of Interlaced Patterns

Figure 23:
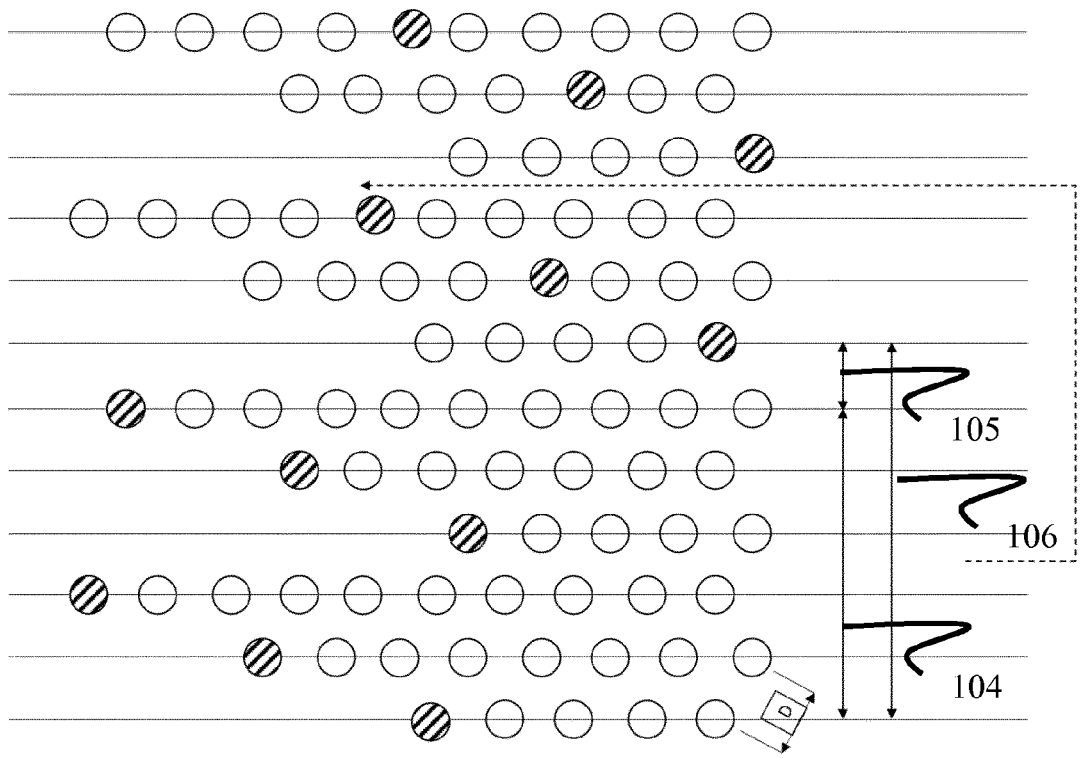

We have described the principle of the use of patterns of laser spots for obtaining a homogeneous arrangement of cavitation bubbles in the treated tissue. These patterns have a particular arrangement of laser spots, including the positioning relatively to each other, and the distances which separate them, give the possibility of observing the constraints discussed above, and notably the minimum distance between each spot in order to avoid interferences, and the maximum distance between each impact point in order to obtain a satisfactory cut out quality of the tissue. The patterns shown up to now, all have the particularity of giving the possibility when a movement is applied to them by the printed sweeping by the scanner, of uniformly and regularly covering a surface of equidistant cavitation bubbles, without leaving untreated areas. At the end of a segment having a regular arrangement of impact points, as indicated in FIG. 23, the scanner controls the displacement of the matrix by a pitch 106 equal to the distance between the rows of the most far away impacts 104, increased by the distance between two contiguous lines 105.

Figure 24:
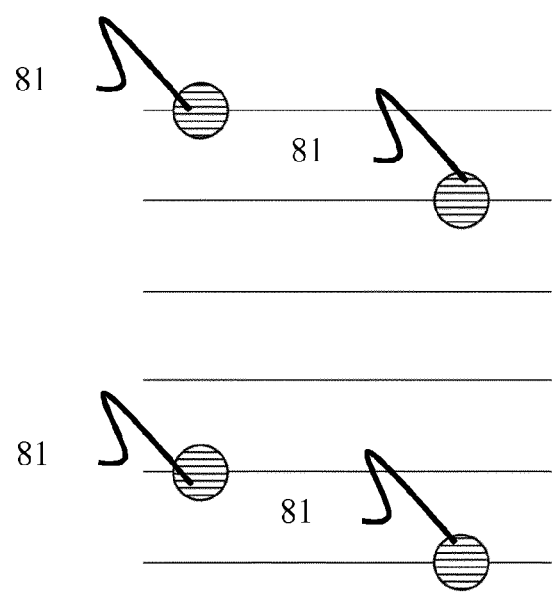
Figure 25:
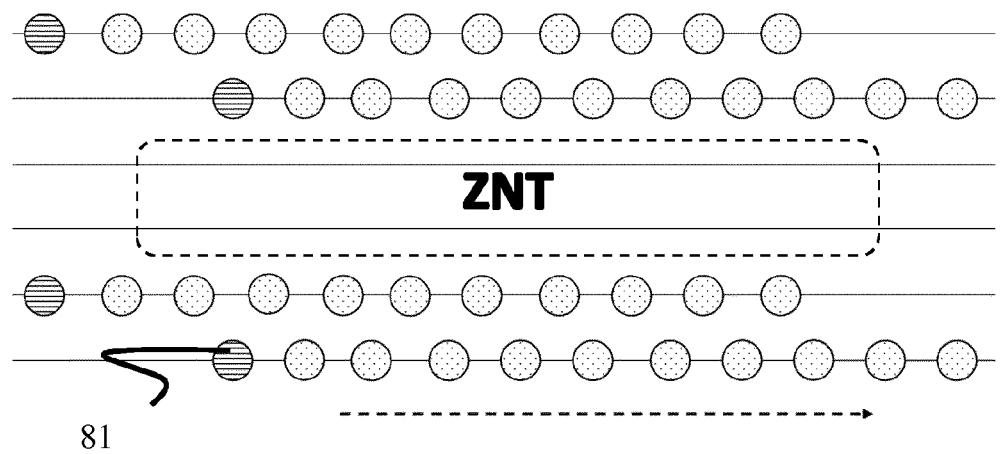
Figure 26:
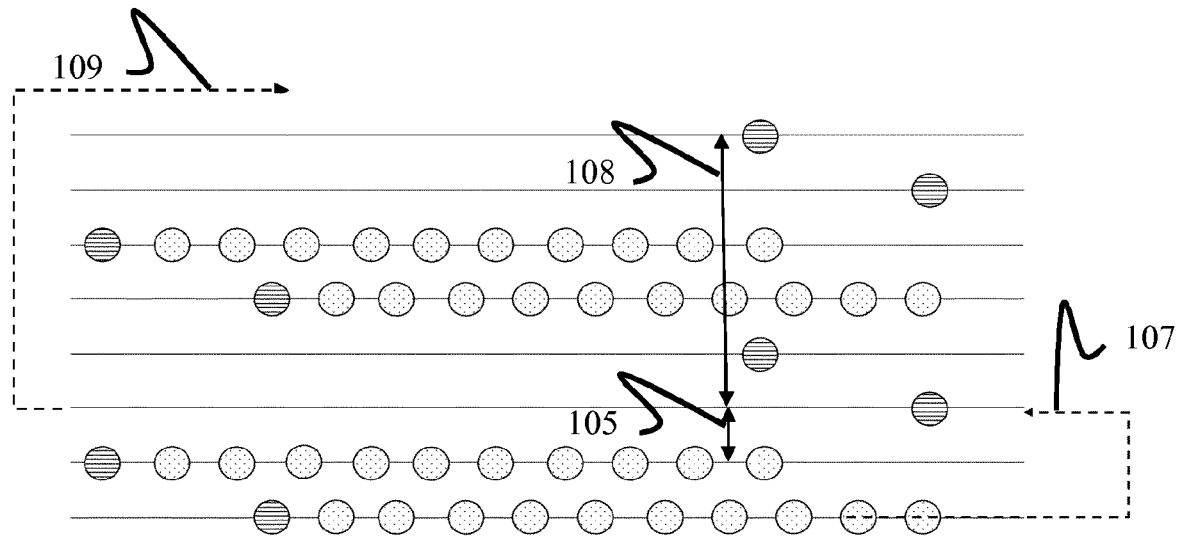
Figure 27:
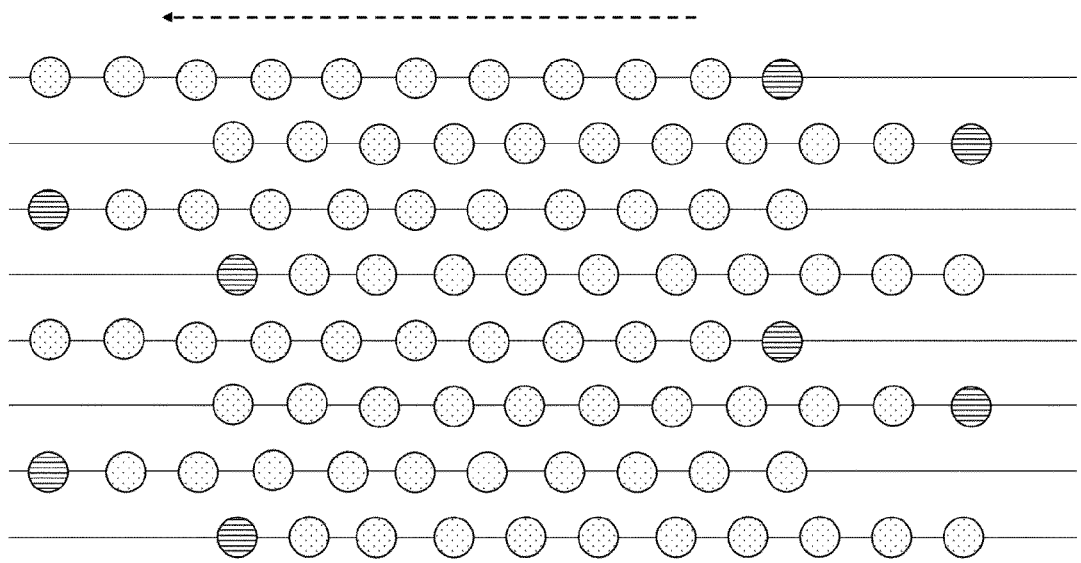

An alternative pattern shown in FIG. 24, gives the possibility of imagining the leaving of an untreated area ZNT as shown in FIG. 25, this ZNT area may be treated with the next sweep with an arrangement of interlaced impact points. For this, the pitch printed by the scanner between two successive segments is not constant and will be for once out of two occurrences equal to twice the distance between two contiguous rows of impacts 107, and once out of two equal to the distance between the farthest impact rows 108, increased by the distance between two contiguous lines 105.

2.6.3.4 Particular Case of a Pattern with a Central Impact Point

Figure 28:
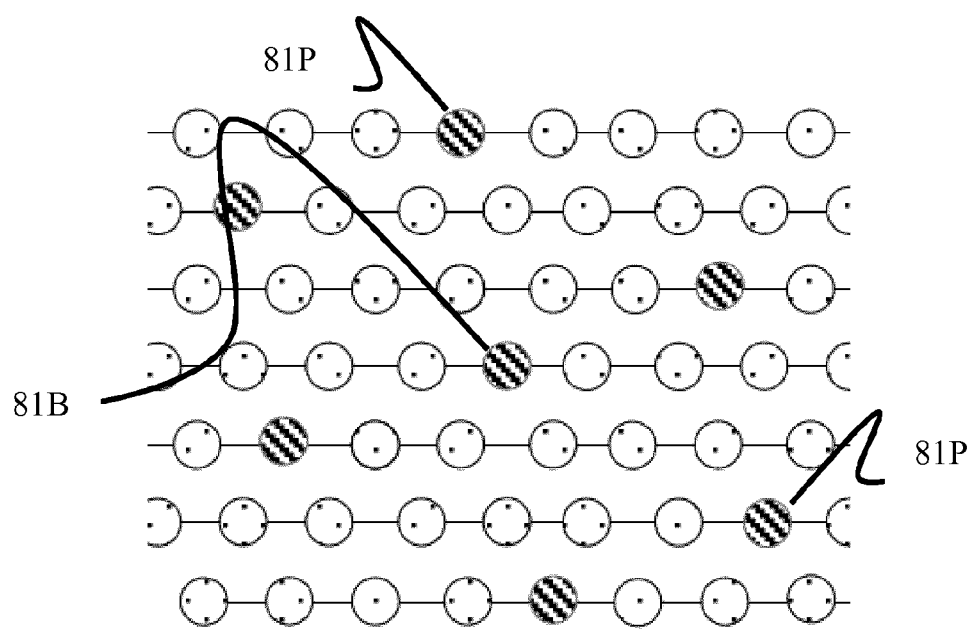

With reference to FIG. 28, another pattern example is illustrated which may be used for cutting-out a tissue. This pattern comprises a plurality (i.e. at least three) of peripheral impact points 81P, and a central impact point 81B positioned at the center of gravity of the pattern, notably in the example illustrated in FIG. 28, at the intersection between diagonal axes passing through opposite peripheral impact points.

The presence of this central impact point gives the possibility of making use of the phenomena generating an energy in the center of the pattern (a phenomenon known under the name of "zero order"). Indeed, during the phase modulation of the L.A.S.E.R. beam 11 with the shaping system 3, a portion of the L.A.S.E.R. beam, stemming from the femtosecond laser is not modulated (because of the existing space between the pixels of the liquid crystals of the SLM). This portion of the non-modulated L.A.S.E.R. beam may induce the generation of an energy peak being formed at the center of the SLM.

When the pattern does not comprise any impact point at this center of gravity, it is necessary to limit this energy peak of zero order in order to avoid untimely generation of cavitation bubbles during the displacement of the pattern in the cutout plane.

2.6.3.5 Remarks

We have described how to position the impact points of a multipoint laser beam, so that the generated bubbles have a homogeneous and regular arrangement on the cutting-out surface of the tissue. From among an infinity of non-regular arrangements, which may also be used, we have demonstrated that in order to obtain a regular arrangement as an equilateral triangle, there existed two types of preferred patterns and that in order to obtain a regular square arrangement, there existed a preferred pattern. For all the preferred matrices, the spacings and angles between each point of the matrix were calculated.

Of course, the invention also deals with any type of pattern for which the impact points are sufficiently spaced apart from each other in order to avoid interferences and the movement of which gives the possibility of obtaining by projection a relatively homogenous cover of the surface to be cut out, even without regular repetition of a geometrical matrix, even if the shown matrices give better results.

Figure 22:
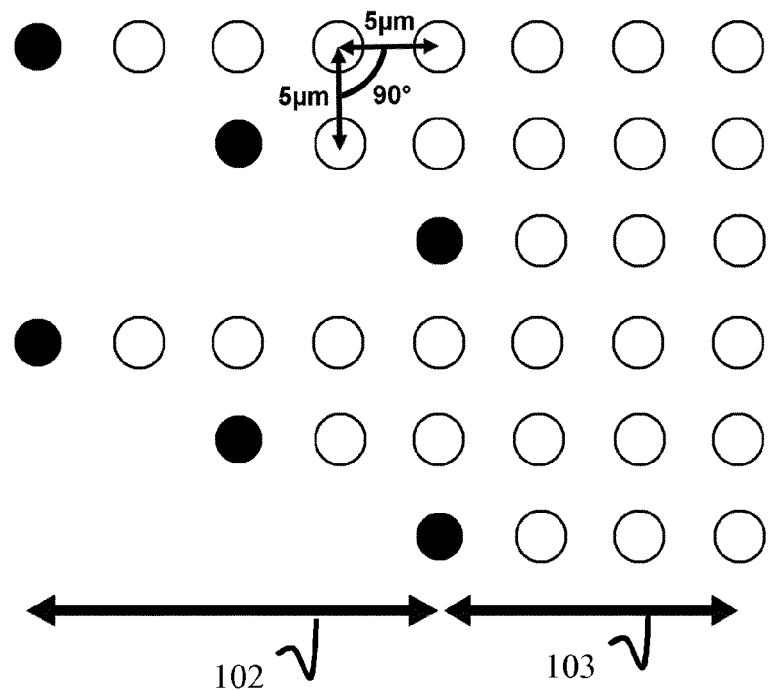

The drawback of this type of pattern shapes is the introduction of an "initiation area" 102 at the periphery of a regular area 103. In this initiation area 102, the cutting-out is incomplete, as illustrated in FIG. 22. Although the size of this initiation area 102 is very small with respect to the global size of the cut out (less than 0.5% of a 8 mm conical cap diameter for the shown examples), this initiation area 102 will preferably have to be as short as possible.

2.6.4 Cutting-Out Device Relative to the Pattern and Associated Process

In summarizing the preceding paragraphs concerning the different characteristics relative to the pattern, the inventors have proposed an apparatus for cutting out human or animal tissue, such as a cornea, or a crystalline, the apparatus including a femtosecond laser capable of sending a L.A.S.E.R. beam in the form of pulses, and a treatment device arranged downstream of the femtosecond laser for processing the L.A.S.E.R. beam generated by the femtosecond laser, the treatment device comprising:

- a shaping system 3 positioned on the trajectory of said beam to modulate the phase of the wave front of the L.A.S.E.R. beam so as to obtain a phase-modulated L.A.S.E.R. beam according to a modulation set value calculated to distribute the energy of the L.A.S.E.R. beam into at least two impact points 81 forming a pattern 8 in its focal plane 21 corresponding to a cutout plane, each impact point producing a cut-out,
- a sweeping optical scanner 4 arranged downstream of the shaping system for shifting the pattern in the cutout plane into a plurality of positions 43 according to a direction of displacement D,
- a control unit including a processor programmed to allow control of the femtosecond laser, the shaping system and the sweeping optical scanner to incline the pattern relative to the direction of displacement such that at least two impact points of the pattern are spaced apart from:
- a non-zero distance according to a first axis parallel to the direction of displacement on the one hand, and
- a non-zero distance according to a second axis perpendicular to the direction of displacement on the other hand.

Advantageously, the pattern can comprise at least two (especially three) adjacent impact points extending along a line of the pattern, the angle between said line of the pattern and the direction of displacement being between 10 and 80°, preferably between 15° and 40°, and even more preferably between 19° and 30°. Also, the pattern can comprise:

- a first set of at least two (especially three) impact points arranged along a first line of the pattern, and
- a second set of at least two (especially three) other impact points arranged along a second line of the pattern parallel to the first line.

The pattern can also comprise at least one other set of impact points arranged along at least one other line of the pattern, parallel to the first and second lines. The impact points of the second set can be offset by a non-zero distance relative to the impact points of the first set. As a variant, each impact point of the second set can be aligned with a respective impact point of the first set according to a straight line perpendicular to the direction of displacement. Advantageously, the distance between two adjacent impact points of the pattern can be greater than 5 µm, preferably greater than 10 µm and even more preferably between 10 and 15 µm. The pattern can also be registered in a surface whereof the ratio between the length and the width is between 1 and 4, preferably between 1 and 2, and even more preferably between 1 and 1.5. Finally, the pattern can comprise a central impact point positioned at the barycenter of the pattern.

The inventors have also proposed a process for controlling a cutting-out apparatus including a femtosecond laser capable of sending a L.A.S.E.R. beam in the form of pulses, and a treatment device arranged downstream of the femtosecond laser for processing the L.A.S.E.R. beam, the treatment device comprising a shaping system and a sweeping optical scanner, the process comprising the steps consisting of:

- modulating, by using the shaping system, the phase of the wave front of the L.A.S.E.R. beam so as to obtain a phase-modulated L.A.S.E.R. beam according to a modulation set value calculated to distribute the energy of the L.A.S.E.R. beam into at least two impact points 81 forming a pattern in its focal plane corresponding to a cutout plane, each impact point producing a cut-out,
- displacing, by using the sweeping optical scanner, the pattern in the cutout plane into a plurality of positions according to a direction of displacement D,
- inclining the pattern relative to the direction of displacement such that at least two impact points of the pattern are spaced apart from:
- a non-zero distance according to a first axis parallel to the direction of displacement on the one hand, and
- a non-zero distance according to a second axis perpendicular to the direction of displacement on the other hand.

Advantageously, the step consisting of modulating can comprise the formation of a pattern comprising at least two (especially three) adjacent impact points extending along a line of the pattern, the angle between said line of the pattern and the direction of displacement being between 10 and 80°, preferably between 15° and 40°, and even more preferably between 19° and 30°. Also, the step consisting of modulating can comprise the formation of a pattern having:

- a first set of at least two (especially three) impact points arranged along a first line of the pattern, and
- a second set of at least two (especially three) other impact points arranged along a second line of the pattern parallel to the first line.

The step consisting of modulating can also comprise the formation of a pattern having at least one other set of impact points arranged along at least one other line of the pattern, parallel to the first and second lines. The step consisting of modulating can also comprise the formation of a pattern wherein the impact points of the second set are offset by a non-zero distance relative to the impact points of the first set. As a variant, the step consisting of modulating can comprise the formation of a pattern wherein each impact point of the second set is aligned with a respective impact point of the first set according to a straight line perpendicular to the direction of displacement.

Advantageously, the step consisting of modulating can comprise the formation of a pattern wherein the distance between two adjacent impact points is greater than 5 µm, preferably greater than 10 µm and even more preferably between 10 and 15 µm.

The step consisting of modulating can also comprise the formation of a pattern registered in a surface whereof the ratio between the length and the width is between 1 and 4, preferably between 1 and 2, and even more preferably between 1 and 1.5. Finally, the step consisting of modulating can also comprise the formation of a pattern having a central impact point positioned at the barycenter of the pattern.

3. Operating Principle

The principle of the operation of the cutting-out apparatus illustrated in FIG. 1 will now be described with reference to the destruction of a lens within the scope of an operation of the cataract. It is quite obvious that the present invention is not limited to the operation of a cataract.

In a first step, the control unit 6:
transmits to the shaping system 3 a first phase mask associated with a first treatment pattern
emits a control signal to the optical focusing system 5 for displacing the focusing plane at a first deep cutout plane in the eye,
activates the displacement of the sweeping optical scanner 4 as far as an initial cutting-out position. The sweeping being accomplished in X, Y, the scanner is equipped with a mirror, X, which allows sweeping along each segment of the displacement path of the pattern, and another mirror Y, which allows, once a segment has been completed, the changing of segment. The mirrors X and Y therefore operate alternately with each other.

When the focusing system 5 and the optical scanner 4 are in position and that the phase mask is loaded into the shaping system 3, the control unit 6 activates the femtosecond laser 1. The latter generates a L.A.S.E.R. beam 11 which crosses the shaping system 3. The shaping system 3 modulates the phase of the L.A.S.E.R. beam. The phase-modulated L.A.S.E.R. beam 31 leaves the shaping system 3 and enters the optical scanner 4 which deviates the modulated L.A.S.E.R. beam 31. The modulated and deviated L.A.S.E.R. beam 41 enters the optical focusing system 5 which focuses the beam in the first cutout plane.

Each impact point 81 of the pattern 8 produces a cavitation bubble. The femtosecond laser 1 continues to emit other pulses as a L.A.S.E.R. beam at a determined rate. Between each pulse, the mirror X has pivoted by a certain angle, which has the consequence of displacing the pattern 8 and of producing new cavitation bubbles shifted relatively to the previous ones, until a line is formed. Thus, a first plurality of cavitation bubbles forming a line is formed in the cutout plane, these bubbles being laid out according to the cutting-out pattern 8. By having the displacement speed of the mirror and/or the generation rate of pulses varied by the femtosecond laser, it is possible to have the distance between two successive patterns varied.

Once this plurality of bubbles forms a complete line, the control unit 6 disables the L.A.S.E.R. source 1, controls the stopping of the pivoting of the mirror X and controls the pivoting of the mirror Y of the optical scanner 4 as far as the next cutting-out position depending on the sweeping pitch of the optical scanner 4, and then again controls the restarting of the pivoting of the mirror X in the opposite direction. When the optical scanner 4 is in position and the mirror X has attained its constant set speed value, the control unit 6 again activates the femtosecond laser 1. The L.A.S.E.R. beam 11 crosses the shaping system 3, the optical scanner 4 and the optical focusing system 5. A second sequence of a plurality of cavitation bubbles is formed in the first cutout plane forming a new line parallel to the previous one and juxtaposed.

These operations are repeated in the whole first cutout plane.

When the optical scanner 4 has swept all the surface of the first cutout plane, a first cutting-out area (the shape and the dimensions of which are controlled by the control unit 6) is generated.

The control unit 6 disables the femtosecond laser 1 and controls:
the translational displacement of the lens(es) of the optical focusing system 5 for displacing the focusing plane 21 in a second cutout plane,
the rotary displacement of the mirror(s) of the optical scanner 4 towards an initial cutting-out position of the second cutout plane,
the optional loading by the shaping system 3 of another phase mask for modifying the positioning and/or the size of the impact points of the pattern, etc.

The control unit 6 repeats the operations for controlling the femtosecond laser 1, the shaping system 3, the sweeping optical scanner 4 and the focusing system 5 in the second cutout plane, and more generally in the successive cutout planes.

At the end of these different steps, a stack of cutout planes is obtained corresponding to the volume to be destroyed 23.

4. Conclusions

Thus, the invention gives the possibility of having an efficient cutting-out tool. The dimensions of the impact points of the pattern being substantially equal (the shape, position and diameter of each spot are dynamically controlled by the calculated phase mask and displayed on the SLM and which may correct the irregularities), the cavitation bubbles which pull to pieces the cut out biological tissues will be of substantially equal sizes. This gives the possibility of improving the quality of the obtained result, with a homogeneous cutout plane, in which the residual tissue bridges all has substantially the same size and which allows dissection by the practitioner of acceptable quality considering the importance of the quality of the surface condition of the cut out tissue when for example this is a cornea.

The invention was described for operations for cutting-out a cornea in the field of ophthalmological surgery, but it is obvious that it may be used for another type of operation in ophthalmological surgery without departing from the scope of the invention. For example, the invention finds application in corneal refractive surgery, such as the treatment of ametropias, notably nearsightedness, farsightedness, astigmatism, in the treatment of loss of accommodation, notably farsightedness.

The invention also finds application in the treatment of cataract with incision of the cornea, cutting-out of the anterior of the lens, and fragmentation of the lens. Finally, in a more general way, the invention relates to all clinical or experimental applications on the cornea or the lens of a human or animal eye.

Still more generally, the invention relates to the vast field of L.A.S.E.R. surgery, and finds an advantageous application when the purpose is to cut out and more particularly vaporize human or animal soft tissues, with a high water content.

The reader will have understood that many modifications may be made to the invention described earlier without materially departing from the novel teachings and advantages described here.

For example, in the different embodiments described earlier, the optical focusing system positioned downstream from the sweeping optical scanner was described as comprising a single module giving the possibility:
- of focusing the modulated and deviated L.A.S.E.R. beam on the one hand, and
- of displacing the focusing plane in different cutout planes on the other hand.

Alternatively, the optical focusing system may consist of two distinct modules each ensuring one of these functions:
- a first module—a so-called "depth positioning module"—positioned upstream from the sweeping optical scanner and allowing displacement of the focusing plane in different cutout planes.
- a second module—a so called "concentrator module" positioned downstream from the sweeping optical scanner and allowing focusing of the modulated and deviated L.A.S.E.R. beam.

Likewise in the different embodiments described earlier, the shaping system described was an SLM. As a variant, the shaping system could be composed of a plurality of phase masks, each phase mask acting on the phase of the L.A.S.E.R. beam to distribute the energy of the L.A.S.E.R. beam by phase modulation according to a pattern distinct. Each phase mask can for example be constituted by a plate (transparent to the L.A.S.E.R. beam) of variable thickness obtained by etching.

In this case, the phase masks can be fixed to a displacement device for shifting each phase mask between:
- an active position in which the phase mask cuts the optical path of the L.A.S.E.R. beam,
- an inactive position in which the phase mask does not extend over the optical path of the L.A.S.E.R. beam The displacement device is for example constituted by a mobile support in rotation around an axis of rotation parallel to the optical path of the L.A.S.E.R. beam, the mobile support being arranged so as to enable the positioning of a respective phase mask on the optical path of the L.A.S.E.R. beam so as to modulate the phase of the latter. But this solution needs mechanical elements to be introduced to the apparatus (displacement device) and therefore does not constitute a preferred solution.

Also, in the description above, the control unit sent a control signal to the shaping system (such as a phase mask in the event where the shaping system is a spatial light modulator) for distributing the energy of the L.A.S.E.R. beam (via phase modulation) into at least two impact points forming a pattern in its focal plane. As a variant, the control unit can be programmed to send several separate control signals for generating patterns different to each other. This modifies the intensity profile of the L.A.S.E.R. beam according to different patterns in the plane of the cut-out, for example to improve the quality of the cut-out in the region of the contours of the cut-out surface in the cutout plane.

Therefore, all the modifications of this type are intended to be incorporated within the scope of the appended claims.

The invention claimed is:

1. An apparatus configured to cut a human or animal tissue, wherein said apparatus includes:
a femtosecond laser configured to send a laser beam in the form of pulses, and
a treatment device adapted for treating the laser beam generated by the femtosecond laser, the treatment device being positioned downstream from said femtosecond laser, the treatment device comprising:
a shaping system positioned on the trajectory of said laser beam, said shaping system including a spatial light modulator configured to display a phase modulation set value and produce a phase—modulated laser single-beam by modulating the phase of the wave front of the laser beam generated by the femtosecond laser,
control means configured to apply the phase modulation set value to the shaping system, wherein the phase modulation set value is calculated by the control means for distributing the energy of the phase—modulated laser single-beam in at least two impact points forming a pattern in a focal plane of said phase—modulated laser single-beam, wherein each impact point generates a cavitation bubble within the human or animal tissue, and wherein an intensity of each impact point will be attenuated at a same time if any portion of the phase-modulated laser single-beam is lost along a propagation path of the phase-modulated laser single beam,
an optical focusing system downstream from the shaping system, the optical focusing system comprising a concentrator module configured to focus the phase—modulated laser single-beam in the focal plane and a depth—positioning module configured to displace the focal plane into a plurality of cutting-out planes, and
a sweeping optical scanner positioned between the concentrator module and the depth—positioning module, said sweeping optical scanner being configured to displace the pattern in the focal plane in a plurality of positions.

2. The apparatus according to claim 1, wherein the treatment device further comprises a control unit configured to control the displacement of the pattern along a displacement path comprising at least one segment in the focal plane.

3. The apparatus according to claim 2, wherein the control unit is configured to control the activation of the femtosecond laser such that a distance between two adjacent positions of the pattern along a segment of the displacement path is greater than or equal to the diameter of an impact point of the pattern.

4. The apparatus according to claim 2, wherein the control unit is adapted to control the displacement of the pattern along a displacement path comprising a plurality of segments, the distance between two adjacent segments of the displacement path being greater than the dimension of the pattern along an axis perpendicular to the plurality of segments.

5. The apparatus according to claim 2, wherein the control unit is configured to control the displacement of the pattern along a displacement path comprising a plurality of parallel segments, the distance between two neighboring segments of the displacement path being constant and less than or equal to 3N times the diameter of an impact point, where N corresponds to the number of impact points of the pattern.

6. The apparatus according to claim 2, wherein the control unit is configured to control the displacement of the pattern along a displacement path comprising a plurality of parallel segments, the distance between at least two neighboring segments being different from the distance between at least two other neighboring segments.

7. The apparatus according to claim 2, wherein the control unit is configured to control the displacement of the pattern along a notch—shaped displacement path in the focal plane.

8. The apparatus according to claim 2, wherein the control unit is configured to control the displacement of the pattern along a spiral—shaped displacement path in the focal plane.

9. The apparatus according to claim 2, wherein the sweeping optical scanner includes at least one optical mirror pivoting around at least two axes, the control unit being configured to control the pivoting of the mirror so as to displace the pattern along the displacement path.

10. The apparatus according to claim 2, which further comprises at least one Dove prism positioned between the shaping system and the sweeping optical scanner.

11. The apparatus according to claim 2, wherein the sweeping optical scanner is configured to operate at a sweeping rate, and wherein the control unit is configured to control the activation of the femtosecond laser, the control unit being configured to activate the femtosecond laser when the sweeping rate of the sweeping optical scanner is greater than a threshold value.

12. The apparatus according to claim 1, which also comprises a filter arranged downstream of the shaping system to block parasite energy generated at the center of the shaping system.

13. The apparatus according to claim 12, wherein the filter comprises a plate including:
- a zone opaque to laser radiation arranged at the center of the plate, and
- a zone transparent to laser radiation extending to the periphery of the opaque zone.

14. The apparatus according to claim 2, the control unit being configured to control the spatial light modulator by emission of at least one control signal, each control signal causing display on the spatial light modulator of a phase mask forming the phase modulation set value.

15. The apparatus according to claim 2, wherein the control unit is configured to control the shaping system, said control unit being adapted to send at least first and second control signals:
- the first control signal causing modulation of the phase of the wave front of the laser beam according to a first modulation set value calculated to distribute the energy of the laser beam into a plurality of first impact points, of the impact points, in the focal plane of the shaping system, the first impact points constituting a first pattern,
- the second control signal causing modulation of the phase of the wave front of the laser beam according to a second modulation set value calculated to distribute the energy of the laser beam into a plurality of second impact points, of the impact points, in the focal plane of the shaping system, the second impact points constituting a second pattern different to the first pattern.

16. The apparatus according to claim 14, wherein the phase modulation set value is a phase mask calculated by using an iterative algorithm based on the Fourier transform.

* * * * *